US012735739B2

(12) United States Patent
André et al.

(10) Patent No.: US 12,735,739 B2
(45) Date of Patent: Sep. 15, 2026

(54) DETERMINATION OF NUCLEIC ACID SEQUENCE CONCENTRATIONS

(71) Applicant: Stilla Technologies, Villejuif (FR)

(72) Inventors: Barbara André, Paris (FR); Rémi Dangla, Paris (FR)

(73) Assignee: Stilla Technologies, Villejuif (FR)

(*) Notice: Subject to any disclaimer, the term of this patent is extended or adjusted under 35 U.S.C. 154(b) by 1101 days.

(21) Appl. No.: 17/768,820

(22) PCT Filed: Oct. 16, 2020

(86) PCT No.: PCT/EP2020/079219

§ 371 (c)(1),
(2) Date: Apr. 13, 2022

(87) PCT Pub. No.: WO2021/074382

PCT Pub. Date: Apr. 22, 2021

(65) Prior Publication Data

US 2024/0093281 A1 Mar. 21, 2024

(30) Foreign Application Priority Data

Oct. 16, 2019 (EP) .................................... 19306346

(51) Int. Cl.
*C12Q 1/6851* (2018.01)
*C12Q 1/686* (2018.01)

(52) U.S. Cl.
CPC ........... *C12Q 1/6851* (2013.01); *C12Q 1/686* (2013.01)

(58) Field of Classification Search
CPC ................ C12Q 1/6851; C12Q 1/6844; C12Q 2531/113; C12Q 2545/10
See application file for complete search history.

(56) References Cited

U.S. PATENT DOCUMENTS

| | | | | |
|---|---|---|---|---|
| 9,892,230 B2 | 2/2018 | Lo et al. | | |
| 11,667,964 B2 * | 6/2023 | Andersen | ............. | C12Q 1/6806 435/6.12 |
| 2002/0028452 A1 * | 3/2002 | Wittwer | ............... | C12Q 1/6851 435/6.12 |
| 2016/0046979 A1 * | 2/2016 | Leamon | ............... | C12Q 1/6855 506/2 |

(Continued)

FOREIGN PATENT DOCUMENTS

| | | |
|---|---|---|
| EP | 2868752 A1 | 5/2015 |
| EP | 3293270 A1 | 3/2018 |

(Continued)

OTHER PUBLICATIONS

Mouliere et al. "High Fragmentation Characterizes Tumour-Derived Circulating DNA", PLOSOne. Sep. 2011, vol. 6, Issue 9 | e23418 (Year: 2011).*

(Continued)

*Primary Examiner* — Eman A Alkafawi
*Assistant Examiner* — Dilara Sultana
(74) *Attorney, Agent, or Firm* — Panitch Schwarze Belisario & Nadel LLP; Erin M. Dunston

(57) ABSTRACT

The present invention relates to a method of determining the concentration of a detected sequence in non-fragmented nucleic acids by applying a correction coefficient to the concentration of said detected sequence measured in fragmented nucleic acids.

19 Claims, 2 Drawing Sheets

Specification includes a Sequence Listing.

(56) References Cited

U.S. PATENT DOCUMENTS

| | | | | |
|---|---|---|---|---|
| 2016/0244827 | A1* | 8/2016 | Türk | G16B 30/00 |
| 2018/0291443 | A1 | 10/2018 | Amorese et al. | |

FOREIGN PATENT DOCUMENTS

| | | | |
|---|---|---|---|
| EP | 3460071 | A1 | 3/2019 |
| JP | 2018196390 | A | 12/2018 |

OTHER PUBLICATIONS

A. Sedlackova et al. "Fragmentation of DNA affects the accuracy of the DNA quantitation by the commonly used methods", Biological Procedures Online 2013, 15:5 (Year: 2013).*

B. Kralik et al. "A Basic Guide to Real time PCR in Microbial Diagnostics: Definitions, Parameters, and Everything", Frontiers in Microbiology, Feb. 2017, vol. 8, article 108. (Year: 2017).*

Japanese Office Action issued in Counterpart Japanese Application No. 2022-522786 (Sep. 10, 2024).

International Preliminary Report on Patentability issued Apr. 19, 2022, for PCT Application No. PCT/EP2020/079219, filed Oct. 16, 2020 6 pages.

International Search Report and Written Opinion, mailed Dec. 23, 2020, for PCT Application No. PCT/EP2020/079219, filed Oct. 16, 2020 6 pages.

Roberts, A. et al. (Mar. 16, 2011). "Improving RNA-Seq Expression Estimates by Correcting for Fragment Bias," Genome Biology 12(3):R22, 14 pages.

Tuerk, A. et al. (May 15, 2017). "Mixture Models Reveal Multiple Positional Bias Types In RNA-Seq Data and Lead to Accurate Transcript Concentration Estimates," Plos Computational Biology 13(5):e1005515, 25 pages.

* cited by examiner

DETERMINATION OF NUCLEIC ACID SEQUENCE CONCENTRATIONS

CROSS REFERENCE TO RELATED APPLICATIONS

This application is a national stage application under 35 U.S.C. § 371 of International Application No. PCT/EP2020/079219, filed internationally on Oct. 16, 2019, which claims priority benefit of European Patent Application No. EP19306346, filed Oct. 16, 2019, the contents of each of which are herein incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 186142001000SEQLIST.TXT, date recorded: Apr. 4, 2022, size: 2,581 bytes).

FIELD OF INVENTION

The present invention pertains to methods of measuring concentrations of nucleic acid sequences in biological samples.

BACKGROUND OF INVENTION

Normal humans have two sets of 23 chromosomes in every healthy, diploid cell. Under some conditions, mutations may occur on any one or more of said chromosomes, leading to chromosomal abnormalities. These abnormalities may be linked to genetic diseases, cancers and other diseases. Detection of chromosomal abnormalities may identify individuals prone to develop a specific disease or define which treatment is most recommended for a given individual. In this regard, testing for chromosomal abnormalities is very valuable.

In addition to human health, detection of chromosomal abnormalities is relevant in additional species including but not limited to insects, bacteria, plants and organic-containing mixed samples, such as soil and food stuffs, where genetically modified organism (GMO) detection due to genetic engineering may be conducted, for example for quality control. The detection of genetic mutations occurring in viruses, viroids and other non-chromosome-containing genomes is also highly pertinent.

In this context, it is relevant to detect the signatures of genome abnormalities, i.e. changes to a specific nucleic acid sequence in a biological sample, in both a qualitative and quantitative manner.

Such detections are currently done efficiently by amplifying target nucleic acids in a sample of interest. Amplification can be carried out by combining oligonucleotide primers with the sample and then subjecting the sample to amplification conditions compatible with nucleic acids quantification, such as polymerase chain reaction (PCR) conditions. These amplification methods enable to generate multiple copies of a single target nucleic acid sequence, thus reaching a detection threshold.

However, measuring the concentration of such specific nucleic acid sequences in a biological sample in a quantitative manner is more relevant, for instance when the objective is not only to detect but also to quantify a genetic disease, for example to monitor the evolution of a rare mutation.

In some cases, nucleic acids present in biological samples are damaged, typically fragmented in sequences of short length. In such populations of fragmented nucleic acids, the sequence to be amplified in a given PCR assay is sometimes randomly cut. In this scenario, amplification of this nucleic acid sequence cannot occur with PCR methods, thus leading to an underestimation of the presence of the nucleic acid sequence of interest.

The present invention proposes a method to correct for such underestimation problems.

BRIEF SUMMARY

This invention relates to a method of determining the concentration of a detected sequence (as defined further below) in non-fragmented nucleic acids, comprising correcting the measured concentration of said detected sequence in the sample comprising fragmented nucleic acids with a correction coefficient, thereby obtaining the concentration of said detected sequence in non-fragmented nucleic acids, wherein the correction coefficient is based on the length distribution (LD) and at least one parameter of the measuring method.

In some embodiments, there is provided a method of determining the concentration of a detected sequence in non-fragmented nucleic acids, comprising the following steps:

i. measuring the concentration of said detected sequence in said sample comprising fragmented nucleic acids with a measuring method; and
ii. correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and at least one parameter of the measuring method.

In some embodiments, there is provided a method of determining the concentration of a detected sequence in non-fragmented nucleic acids, comprising the following steps:

i. determining a length distribution (LD) of nucleic acids in a sample comprising fragmented nucleic acids, wherein the fragmented nucleic acids are derived from said non-fragmented nucleic acids;
ii. measuring the concentration of said detected sequence in said sample comprising fragmented nucleic acids with a measuring method; and
iii. correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and at least one parameter of the measuring method.

In some embodiments, the method comprises:

i. providing a sample of fragmented nucleic acids, said fragmented nucleic acids being derived from said non-fragmented nucleic acids;
ii. providing the nucleic acid fragments length distribution (LD) of said fragmented nucleic acids;
iii. measuring the concentration of said detected sequence in said sample of fragmented nucleic acids with a measuring method;

iv. determining a correction coefficient depending on said nucleic acid fragments length distribution (LD) of said fragmented nucleic acids and on parameters of said measuring method; and v. correcting the concentration of said detected sequence in the fragmented nucleic acids with said correction coefficient to obtain the concentration of said detected sequence in non-fragmented nucleic acids.

In an embodiment, the sample of fragmented nucleic acids is any combination of the following three categories:

i. either a cell-free sample or a cell-containing sample;

ii. either a naturally fragmented sample or an artificially fragmented sample; and iii. any type of deoxyribonucleic acid (DNA) or ribonucleic acid (RNA).

In an embodiment, the measuring method is an isothermal quantitative nucleic acid amplification method, preferably selected from loop mediated isothermal amplification and quantitative nucleic acid sequence-based amplification.

In another embodiment, the measuring method is a non-isothermal quantitative nucleic acid amplification method, preferably selected from quantitative Polymerase Chain Reaction, real time Polymerase Chain Reaction, digital Polymerase Chain Reaction, multiplex Polymerase Chain Reaction and multiplex digital Polymerase Chain Reaction.

In an embodiment, the parameters of said measuring method include the length of the sequence to be amplified, as further defined below. In a specific configuration of this embodiment, at least 5% of nucleic acid fragments have a length shorter than the length of the sequence to be amplified. In another specific configuration of this embodiment, at most 95% of nucleic acid fragments have a length shorter than the length of the sequence to be amplified.

In an embodiment, the length of the sequence to be amplified is longer than 40 bp and shorter than 200 bp, preferably longer than 50 bp and shorter than 170 bp, more preferably longer than 65 bp and shorter than 150 bp, even more preferably longer than 70 bp and shorter than 130 bp.

In an embodiment, the nucleic acid fragments length distribution (LD) is comprised in the range of from 25 bp to 350 bp, preferably from 30 bp to 320 bp, more preferably from 35 bp to 290 bp, even more preferably from 40 bp to 270 bp.

This invention further relates to a method of determining a function of a first concentration of a first detected sequence $S_1$ and of a second concentration of a second detected sequence $S_2$ in non-fragmented nucleic acids comprising the following steps:

i. determining the concentration of $S_1$ in said non-fragmented nucleic acids according to any determination method described above;

ii. determining the concentration of $S_2$ in said non-fragmented nucleic acids according to any determination method described above; and iii. computing said function of said $S_1$ concentration and said $S_2$ concentration;

wherein said $S_1$ concentration and said $S_2$ concentration are determined in the same sample; and wherein the length of the sequence to be amplified associated with $S_1$ is different from the length of the sequence to be amplified associated with $S_2$.

This invention also relates to a system configured to determine the concentration of a detected sequence in non-fragmented nucleic acids comprising:

i. a module configured to measure the concentration of said detected sequence in a sample of fragmented nucleic acids, said fragmented nucleic acids being derived from said non-fragmented nucleic acids;

ii. a module configured to compute a correction coefficient depending on nucleic acid fragments length distribution (LD) of said fragmented nucleic acids and on parameters of said measure; and iii. a module configured to compute the concentration of said detected sequence in non-fragmented nucleic acids with said correction coefficient.

In a specific configuration, the module configured to measure the concentration of said detected sequence in said fragmented nucleic acids is an isothermal quantitative nucleic acid amplification module, preferably selected from loop mediated isothermal amplification module and quantitative nucleic acid sequence-based amplification module.

In an alternative configuration, the module configured to measure the concentration of said detected sequence in said fragmented nucleic acids is a non-isothermal quantitative nucleic acid amplification module, preferably selected from quantitative Polymerase Chain Reaction module, real time Polymerase Chain Reaction module, digital Polymerase Chain Reaction module, multiplex Polymerase Chain Reaction module and multiplex digital Polymerase Chain Reaction.

In an embodiment, parameters of said measure include the length of the sequence to be amplified.

Definitions

In the present invention, the following terms have the following meanings:

The term "amplicon" refers to a nucleic acid product of an amplification reaction. An amplicon may be single-stranded or double-stranded, or a combination thereof.

The term "amplification" refers to a reaction in which replication occurs repeatedly over time to form multiple copies of at least one segment of a template molecule. Amplification may generate an exponential or linear increase in the number of copies as amplification proceeds. Typical amplifications produce a greater than 1,000-fold increase in copy number and/or signal. Exemplary amplification reactions for the droplet-based assays disclosed herein may include the polymerase chain reaction (PCR) or ligase chain reaction, each of which is driven by thermal cycling. The droplet-based assays also or alternatively may use other amplification reactions, which may be performed isothermally. Amplification may be performed, or assayed for its occurrence, in an amplification mixture, which is any composition capable of generating multiple copies of a nucleic acid target molecule, if present, in the composition. An "amplification mixture" may include any combination of at least one primer or primer pair, at least one probe, at least one replication enzyme (e.g., at least one polymerase, such as at least one DNA and/or RNA polymerase such as reverse transcriptase), and deoxynucleotide (and/or nucleotide) triphosphates (dNTPs and/or NTPs) and a buffer containing any ingredients essential to the replication enzymes activity, among others.

The term "assay" refers to a procedure(s) and/or reaction(s) used to characterize a sample, and any signal(s), value(s), data, and/or result(s) obtained from the procedure(s) and/or reaction(s).

The term "cut" is equivalent to the term "fragmented", referring to nucleic acid sequences.

The term "detected sequence" refers to the precise sequence being quantified from the sample in the method of the invention. In the case of a point mutation, the detected sequence includes the mutation being detected. In some embodiments, a fluorescent reporter is used. When a fluorescent reporter linked to a specific sequence is used (e.g. as illustrated in FIG. 1A), the "detected sequence" may be shorter than and contained within the sequence to be amplified (as further defined herein). When a free fluorescent reporter is used (e.g. as illustrated in FIG. 1B), the detected sequence usually is the amplicon.

The term "digital PCR" or "dPCR" refers to a PCR assay performed in partitions of a sample to determine the presence/absence, concentration, and/or copy number of a nucleic acid target in the sample, based on how many of the sample partitions support amplification of the target. The concept of digital PCR may be extended to other types of analytes, besides nucleic acids.

The term "label" refers to an identifying and/or distinguishing marker or identifier connected to or incorporated into any entity, such as a compound, biological particle (e.g., a cell, bacteria, spore, virus, or organelle), or droplet. A label may, for example, be a dye that renders an entity optically detectable and/or optically distinguishable. Exemplary dyes used for labeling are fluorescent dyes (fluorophores) and fluorescence quenchers.

The term "length" in association with nucleic acid refers to the number of sequential nucleotides or bases forming a single stranded molecule or the number of sequential base pairs forming a double stranded molecule. Length is measured in nucleotides and base pairs.

The term "multiplex digital PCR" refers to a digital PCR assay performed to amplify at least two different nucleic acid sequences simultaneously, in particular two, three, four, five, six, seven, height or more different nucleic acid sequences simultaneously (as if performing many separate PCR reactions all together in one single pot). This process amplifies nucleic acids in samples using multiple primers. In particular, "multiplex digital PCR" includes "duplex digital PCR" and "triplex digital PCR". By opposition, a digital PCR assay performed to amplify one nucleic acid sequence is "simplex digital PCR", often shortened in "digital PCR".

The term "multiplex PCR" refers to a PCR assay performed to amplify at least two different nucleic acid sequences simultaneously in particular two, three, four, five, six, seven, height or more different nucleic acid sequences simultaneously (as if performing many separate PCR reactions all together in one single pot). This process amplifies nucleic acids in samples using multiple primers. In particular, "multiplex PCR" includes "duplex PCR" and "triplex PCR". By opposition, a PCR assay performed to amplify one nucleic acid sequence is "simplex PCR", often shortened in "PCR".

The term "nucleic acid" refers to both deoxyribonucleic acid (DNA) or ribonucleic acid (RNA), whether it be a product of amplification, synthetically created, a product of reverse transcription of RNA or naturally occurring. Typically, nucleic acids are single- or double-stranded molecules and are composed of naturally occurring nucleotides.

The term "nucleotide" in addition to referring to the naturally occurring ribonucleotide or deoxyribonucleotide monomers, shall herein be understood to refer to related structural variants thereof, including derivatives and analogs and chemical modifications, that are functionally equivalent with respect to the particular context in which the nucleotide is being used (e.g., hybridization to a complementary base: Adenine (A) pairs to Thymine (T) and Guanine (G) pairs to Cytosine (C)), unless the context clearly indicates otherwise.

The term "partition" refers to a separated portion of a bulk volume. The partition may be a sample partition generated from a sample, such as a prepared sample, that forms the bulk volume. Partitions generated from a bulk volume may be substantially uniform in size or may have distinct sizes (e.g., sets of partitions of two or more discrete, uniform sizes). Exemplary partitions are "droplets". Partitions may also vary in size with a predetermined size distribution or with a random size distribution.

The term "PCR" or "polymerase chain reaction" refers to a nucleic acid amplification assay that relies on alternating cycles of heating and cooling (i.e., thermal cycling) to achieve successive rounds of replication. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. Other forms of PCR such as Touchdown PCR can be included in this definition where the annealing and/or extension temperature may change during the cycling reaction.

The term "primer" refers to an oligonucleotide capable of acting as a point of initiation of template-directed nucleic acid synthesis when placed under conditions in which polynucleotide extension is initiated; e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction).

The term "probe" refers to a nucleic acid connected to at least one label, such as at least one dye.

The term "qualitative PCR" refers to a PCR-based analysis that determines whether or not a target is present in a sample, generally without any substantial quantification of target presence. In exemplary embodiments, digital PCR that is qualitative may be performed by determining whether a packet of partitions contains at least a predefined percentage of positive droplets (a positive sample) or not (a negative sample).

The terms "quantitative PCR", "qPCR", "real-time quantitative polymerase chain reaction" or "kinetic polymerase chain reaction" refer to a PCR-based analysis that determines a concentration and/or copy number of a target in a sample. This technique simultaneously amplifies and quantifies target nucleic acids using PCR wherein the quantification is by virtue of an intercalating fluorescent dye that are only detectable once hybridized to a target nucleic acid or sequence-specific probes containing fluorescent reporter molecules that are only detectable upon sequence amplification.

The term "real time PCR" refers to a PCR-based analysis in which amplicon formation is measured during the reaction, such as after completion of one or more thermal cycles prior to the final thermal cycle of the reaction. Real-time PCR generally provides quantification of a target based on the kinetics of target amplification.

The term "replication" refers to a process forming a copy (i.e., a direct copy and/or a complimentary copy) of a nucleic acid or a segment thereof. Replication generally involves an enzyme, such as a polymerase and/or a ligase, among others. The nucleic acid and/or segment replicated is a template (and/or a target) for replication.

The term "sample" refers to a compound, composition, and/or mixture of interest, from any suitable source(s). A sample is the general subject of interest for an assay that analyzes an aspect of the sample, such as an aspect related to at least one analyte that may be present in the sample. Samples may be analyzed in their natural state, as collected, and/or in an altered state, for example, following storage, preservation, extraction, lysis, dilution, concentration, purification, filtration, mixing with one or more reagents, preamplification (e.g., to achieve target enrichment by performing limited cycles (e.g., <15) of PCR on sample prior to PCR), removal of amplicon (e.g., treatment with uracil-d-glycosylase (UDG, also known as UNG, uracil-N-glycosylase gene) prior to PCR to eliminate any carry-over contamination by a previously generated amplicon (i.e., the amplicon is digestable with UDG because it is generated with dUTP instead of dTTP)), partitioning, or any combination thereof, among others. Clinical samples may include nasopharyngeal wash, blood, plasma, cell-free plasma, buffy coat, saliva, urine, stool, sputum, mucous, wound swab, tissue biopsy, milk, a fluid aspirate, a swab (e.g., a nasopharyngeal swab), and/or tissue, among others. Samples may be collected for diagnostic purposes (e.g., the quantitative measurement of a clinical analyte such as an infectious agent) or for monitoring purposes (e.g., to determine whether an environmental analyte of interest such as a bio-threat agent has exceeded a predetermined threshold).

The term "sequence to be amplified" refers to the nucleic acid that includes the "detected sequence" (as defined above), starting with the sequence of the forward primer, ending with the sequence complementary to the reverse primer, and containing any additional base pairs positioned in-between the primer sequences. The product of the amplification of the sequence to be amplified is the amplicon. Ultimately, amplification allows quantification of the "sequence to be amplified" by determination of concentration. The length of the sequence to be amplified is noted "$L_a$".

BRIEF DESCRIPTION OF THE DRAWINGS

FIG. 1 is a schematic representation of quantitative nucleic acid amplification methods, by way of example and not limitation. Here, the double-stranded fragmented nucleic acids are represented by horizontal solid black lines. Two primers (forward primer FP and reverse primer RP) define the left and right borders, respectively, of the sequence to be amplified (SA). Both strands of the sequence to be amplified (SA) are copied during amplification.

DETAILED DESCRIPTION

Figure 1A:
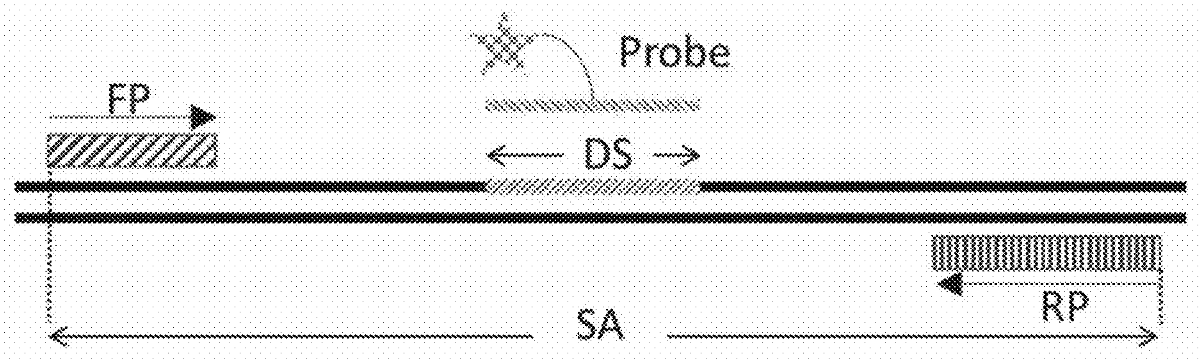
In FIG. 1A, the detected sequence (DS) is a part of the sequence to be amplified (SA). A fluorescently-labeled probe (Probe) binds specifically to the detected sequence.

The present application provides methods and systems for correcting the measured concentration of a detected sequence in a nucleic acid sample comprising fragmented nucleic acids. The methods and systems provided herein allow determination of a corrected concentration of the detected sequence that more closely approximates the true concentration of the detected sequence in non-fragmented nucleic acids. When the concentration of a detected sequence is measured by amplification of a sequence to be amplified comprising the detected sequence, fragments containing part of the sequence to be amplified but with a length shorter than the length of the sequence to be amplified will not be replicated. This failure to replicate the truncated target region (i.e., sequence to be amplified) leads to an underestimation of the concentration. The methods provided herein can be applied to correct for the resulting underestimation of the concentration of the nucleic acid in the non-fragmented nucleic acid sample.

This invention thus in some aspects provides a method of determining the concentration of a detected sequence (including determining the number of copies of said detected sequence) in non-fragmented nucleic acids comprising the following steps (hereinafter referred to as "basic method"). In some aspects, the invention provides a method of calibrating the concentration of a detected sequence (including the number of copies of said detected sequence) in a sample comprising fragmented nucleic acid molecules. Also provided are kits, software, devices, and other articles of manufacture useful for the methods described herein.

I. METHODS OF THE PRESENT APPLICATION

This invention relates to a method of determining the concentration of a detected sequence in non-fragmented nucleic acids, comprising correcting the measured concentration of said detected sequence in the sample comprising fragmented nucleic acids with a correction coefficient, thereby obtaining the concentration of said detected sequence in non-fragmented nucleic acids, wherein the correction coefficient is based on the length distribution and at least one parameter of the measuring method.

In some embodiments, there is provided a method of determining the concentration of a detected sequence in non-fragmented nucleic acids, comprising the following steps:

i. measuring the concentration of said detected sequence in said sample comprising fragmented nucleic acids with a measuring method; and
ii. correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and at least one parameter of the measuring method.

In some embodiments, there is provided a method of determining the concentration of a detected sequence (as defined further below) in non-fragmented nucleic acids, comprising the following steps:

i. amplifying a target region (hereafter referred to as "a sequence to be amplified") comprising said detected sequence in said sample comprising fragmented nucleic acids;
ii. measuring the concentration of said detected sequence; and
iii. correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and at least one parameter of the measuring method.

In some embodiments, provided herein is a method of determining the concentration of a detected sequence in non-fragmented nucleic acids comprising the following steps:

i. determining a length distribution (LD) of nucleic acids in a sample comprising fragmented nucleic acids, wherein the fragmented nucleic acids are derived from said non-fragmented nucleic acids;

ii. measuring the concentration of said detected sequence in said sample comprising fragmented nucleic acids with a measuring method; and correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and at least one parameter of the measuring method.

In some embodiments, provided herein is a method of calibrating a measured concentration of a detected sequence in a sample comprising fragmented nucleic acids, such that it more closely reflects the concentration of the detected sequence in non-fragmented nucleic acids, comprising the following steps:

i. determining a length distribution (LD) of nucleic acids in a sample comprising fragmented nucleic acids, wherein the fragmented nucleic acids are derived from said non-fragmented nucleic acids; and ii. correcting the measured concentration with a correction coefficient to obtain the concentration of said detected sequence in non-fragmented nucleic acids, wherein the correction coefficient is based on the length distribution (LD) and at least one parameter of a measuring method used to determine the concentration of the detected sequence.

In some embodiments, provided herein is a method of calibrating a measured concentration of a detected sequence in a sample comprising fragmented nucleic acids, wherein the measured concentration of the detected sequence is an underestimation of the real concentration of the detected sequence in the sample, comprising the following steps:

i. determining a length distribution (LD) of nucleic acids in a sample comprising fragmented nucleic acids, wherein the fragmented nucleic acids are derived from said non-fragmented nucleic acids; and ii. correcting the measured concentration with a correction coefficient to obtain the concentration of said detected sequence in non-fragmented nucleic acids, wherein the correction coefficient is based on the length distribution (LD) and at least one parameter of a measuring method used to determine the concentration of the detected sequence.

In some embodiments, provided herein is a method of correcting the measured concentration of a detected sequence in a sample comprising fragmented nucleic acids, such that it more closely reflects the concentration of the detected sequence in non-fragmented nucleic acids, comprising the following steps:

i. determining a length distribution (LD) of nucleic acids in a sample comprising fragmented nucleic acids, wherein the fragmented nucleic acids are derived from said non-fragmented nucleic acids;

ii. measuring the concentration of said detected sequence in said sample comprising fragmented nucleic acids with a measuring method;

and iii. correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and at least one parameter of the measuring method.

In some embodiments, provided herein is a method of correcting the measured concentration of a detected sequence in a sample comprising fragmented nucleic acids, wherein the measured concentration of the detected sequence is an underestimation of the real concentration of the detected sequence in the sample, comprising the following steps:

i. determining a length distribution (LD) of nucleic acids in a sample comprising fragmented nucleic acids, wherein the fragmented nucleic acids are derived from said non-fragmented nucleic acids;

ii. measuring the concentration of said detected sequence in said sample comprising fragmented nucleic acids with a measuring method;

and iii. correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and at least one parameter of the measuring method.

The methods of the present application in some embodiments do not comprise obtaining the sequence of the fragmented nucleic acids. In some embodiments, the methods do not comprise obtaining or predicting the genetic coordinates of the fragmented nucleic acids. In some embodiments, the method does not comprise assembly of the fragmented nucleic acids into a contiguous sequence.

The sample of fragmented nucleic acids in some embodiments is in any combination of the following three categories, as described in the "Nucleic acid sample and length distribution" subsection below:

i. either a cell-free sample or a cell-containing sample;

ii. either a naturally fragmented sample or an artificially fragmented sample; and iii. any type of deoxyribonucleic acid or ribonucleic acid.

In some embodiments, the measuring method does not comprise sequencing the nucleic acids in the sample. In some embodiments, measuring of the concentration of the detected sequence can comprise amplifying a sequence to be amplified comprising the detected sequence. In some embodiments, the measuring method is an isothermal quantitative nucleic acid amplification method (e.g., loop-mediated isothermal amplification or quantitative nucleic acid sequence-based amplification). In some embodiments, the measuring method is a non-isothermal quantitative nucleic acid amplification method (e.g. quantitative Polymerase Chain Reaction, real time Polymerase Chain Reaction, digital Polymerase Chain Reaction, multiplex Polymerase Chain Reaction and multiplex digital Polymerase Chain Reaction).

Figure 1B:
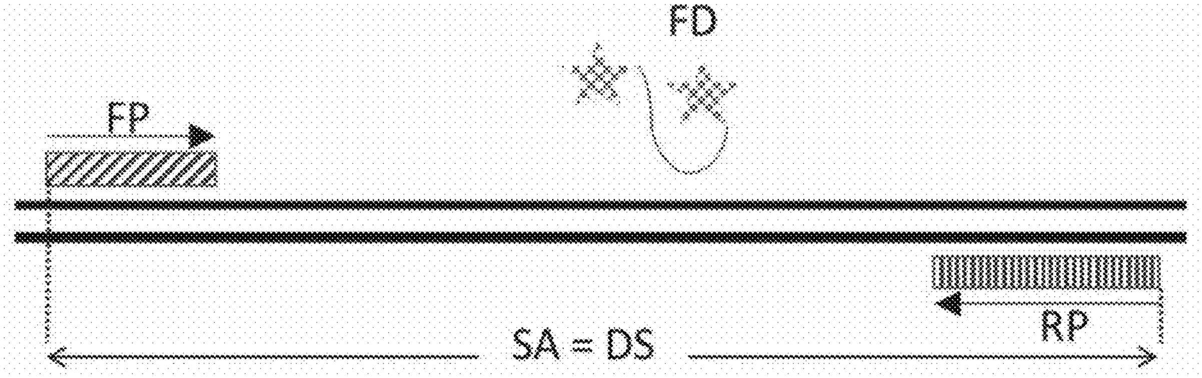
In FIG. 1B, the detected sequence (DS) and the sequence to be amplified (SA) are the same. A fluorescent dye (FD) is intercalated in double-stranded nucleic acids produced during amplification.

In some embodiments according to any of the preceding methods, the detected sequence and the sequence to be amplified are the same, and the step of measuring comprises detecting incorporation of a label in nucleic acids produced during amplification (e.g., an intercalating dye, such as a fluorescent dye comprising a fluorophore), as shown in FIG. 1B.

In some embodiments, the detected sequence is a subset of the sequence to be amplified, and/or the step of measuring comprises detecting binding of a labeled probe to the detected sequence (e.g., a fluorescently labeled probe comprising a fluorophore), as shown in FIG. 1A.

The measuring method implemented in the measuring step of the basic method of the invention intrinsically uses some parameters relevant to determine the correction coefficient. In a particular embodiment, the measuring method is an amplification method using replication and an amplification mixture.

In some embodiments, the method can further comprise the step of determining the correction coefficient based on the length distribution of nucleic acids in the sample and at least one parameter of said measuring method.

In some embodiments, the at least one parameter of the measuring method can comprise length of the sequence to be amplified. In some embodiments, the at least one parameter of the measuring method only comprises the length of the sequence to be amplified.

Thus, for example, in some embodiments, provided herein is a method of determining the concentration of a detected sequence in non-fragmented nucleic acids comprising the following steps:

i. determining a length distribution (LD) of nucleic acids in a sample comprising fragmented nucleic acids, wherein the fragmented nucleic acids are derived from said non-fragmented nucleic acids;

ii. measuring the concentration of said detected sequence in said sample comprising fragmented nucleic acids with a measuring method; and correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and the length of a sequence to be amplified comprising the detected sequence.

In some embodiments, provided herein is a method of calibrating a measured concentration of a detected sequence in a sample comprising fragmented nucleic acids, such that it more closely reflects the concentration of the detected sequence in non-fragmented nucleic acids, comprising the following steps:

i. determining a length distribution (LD) of nucleic acids in a sample comprising fragmented nucleic acids, wherein the fragmented nucleic acids are derived from said non-fragmented nucleic acids; and ii. correcting the measured concentration with a correction coefficient to obtain the concentration of said detected sequence in non-fragmented nucleic acids, wherein the correction coefficient is based on the length distribution (LD) and the length of a sequence to be amplified comprising the detected sequence.

In some embodiments, provided herein is a method of correcting the measured concentration of a detected sequence in a sample comprising fragmented nucleic acids, such that it more closely reflects the concentration of the detected sequence in non-fragmented nucleic acids, comprising the following steps:

i. determining a length distribution (LD) of nucleic acids in a sample comprising fragmented nucleic acids, wherein the fragmented nucleic acids are derived from said non-fragmented nucleic acids;

ii. measuring the concentration of said detected sequence in said sample comprising fragmented nucleic acids with a measuring method; and iii. correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and the length of a sequence to be amplified comprising the detected sequence.

The length of the sequence to be amplified can be denoted as $L_a$, which is actually the sum of the length of the primers (forward and reverse) plus the length of any additional base pairs located between the primers.

In an embodiment, the length of the sequence to be amplified $L_a$ is equal to or longer than the length of the primers (forward and reverse), and in some embodiments is no longer than about 200 bp, for example no longer than about 170 bp, no longer than 150 bp, or no longer than 130 bp.

For replication, the primer has first to bind to a nucleic acid. Binding is optimal when all the bases of the primer are complementary to the nucleic acid (for DNA Adenine is complementary to Thymine and Guanine is complementary to Cytosine; for RNA Adenine is complementary to Uracil and Guanine is complementary to Cytosine), but binding may also be efficient if a few bases of the primer are not complementary with the nucleic acid. In other words, if the nucleic acid sequence is shortened by a few bases where the primer should bind, the replication process can still be efficient. A relevant parameter may be $L_a$, or $L_a-n$ with n an integer greater than 0, or $r \cdot L_a$ (r multiplied by $L_a$) with a shortening coefficient r ranging between 75% and 100% and with the proviso that $r \cdot L_a$ is always an integer value. In some embodiments, n is an integer from 1 to 15, 1 to 10, or 1 to 5. In some embodiments, r is a value greater than 0.75 and less than 1, greater than 0.8 and less than 1, greater than 0.85 and less than 1, greater than 0.9 and less than 1, or greater than 0.95 and less than 1.

With the length parameter $L_a$, the correction coefficient may be determined according to any of the embodiments described in the "Determining a correction coefficient" sub section below.

The correction coefficient may be computed similarly with $L_a-n$ with n an integer greater than 0 (e.g., from 1 to 15, 1 to 10, or 1 to 5) or $r \cdot L_a$ (r multiplied by $L_a$) with a shortening coefficient r ranging between 75% and 100% and with the proviso that $r \cdot L_a$ is always an integer value to take into account shortened fragments still leading to replication, as described in the "Determining a correction coefficient" subsection below.

In some embodiments, there is provided a method of determining the concentration of a detected sequence in non-fragmented nucleic acids comprising the following steps: i. determining a length distribution of nucleic acids in a sample comprising fragmented nucleic acids, wherein the fragmented nucleic acids are derived from said non-fragmented nucleic acids; ii. measuring the concentration of said detected sequence in said sample comprising fragmented nucleic acids with a measuring method; and iii. correcting the measured concentration of said detected sequence in the sample comprising fragmented nucleic acids with a correction coefficient to obtain the concentration of said detected sequence in non-fragmented nucleic acids, wherein the correction coefficient is determined by:

$$\frac{1}{\frac{1}{\hat{l}}[(\Sigma_{i=L}^{\infty} i f(i)) + (1 - L)\Sigma_{i=L}^{\infty} f(i)]};$$

wherein L is ($L_a$–n) or r*$L_a$, wherein $L_a$ is the length of the sequence to be amplified, wherein n is an integer greater than 0 and less than 15;

wherein r is between 0.75 and 1;

wherein f(i) is the probability that a fragment in the sample has a length of i base pairs; and wherein $$\hat{l} = \sum_{i=1}^{\infty} \text{if}(i)$$

is the average length of the nucleic acid fragments.

In some embodiments, L is $L_a$.

With regards to the length distribution of nucleic acid fragments, fragments with a length shorter than $L_a$ (or $L_a$–n or r·$L_a$) will not be replicated anyway. If such fragments contain a part of the sequence to be amplified, it will not be replicated and this leads to an underestimation of the concentration.

The correction coefficient described herein can also be based on the probability that the sequence to be amplified is fragmented based on sequence fragmentation bias. In some embodiments, the relative probability that a sequence to be amplified will be fragmented is known. In some embodiments, the probability that the sequence to be amplified will be fragmented depends on the source of fragmentation (e.g., naturally-occurring nucleic acid fragmentation or fragmentation by physical means such as sonication). For example, the correction coefficient can be adjusted by multiplying the correction coefficient prior to adjustment with a probability that the sequence to be amplified is fragmented based on sequence fragmentation bias. Alternatively, the probability of that the sequence to be amplified is fragmented based on sequence fragmentation bias can be accounted for by modifying the fragmentation length distribution (LD) curve.

In some embodiments, the at least one parameter of the measuring method further comprises a parameter of the amplifying step selected from the group consisting of: GC content of the sequence to be amplified; GC content of the amplification primers; length of the amplification primers; type of polymerase being used; and temperature of the amplification cycles. In some embodiments, the additional parameter of the amplifying step can be incorporated as a coefficient multiplied by the fragment length distribution (LD) curve, or as a calibration coefficient multiplied by the correction coefficient as described in the "Calibrating the correction coefficient" subsection below.

In some embodiments, the at least one parameter of the measuring method further comprises a parameter of the measuring step selected from the group consisting of: sequence of a detecting probe; photostability of a fluorophore used; chemical stability of a fluorophore used; quantum yield of a fluorophore used; and wavelength of a fluorophore used. In some embodiments, the additional parameter of the amplifying step can be incorporated as a coefficient multiplied by the fragment length distribution (LD) curve, or as a calibration coefficient multiplied by the correction coefficient as described in the "Calibrating the correction coefficient" subsection below.

In some embodiments, the correcting comprises multiplying the concentration measured in the sample comprising fragmented nucleic acids with the correction coefficient. In some embodiments, the correcting comprises multiplying the concentration measured in the sample comprising fragmented nucleic acids with the correction coefficient and an additional correction factor. In some embodiments, the additional correction factor is based on the probability that the sequence to be amplified is fragmented based on sequence fragmentation bias. In some embodiments, the additional correction factor is based on at least one parameter of the measuring method, as described above. In some embodiments, the additional correction factor is based on at least one parameter of the measuring method affecting sequence amplification (e.g., GC content of the sequence to be amplified). In some embodiments, the additional correction factor is based on at least one parameter of the measuring method affecting detection of the detected sequence (e.g., photostability or chemical stability of the fluorophore used). In some embodiments, the additional correction factor is based on an experimentally determined calibration factor, as described in the "Calibrating the correction coefficient" subsection below.

In some embodiments, the correcting is applied if at least 5% of the nucleic acids in the sample have a length shorter than the length of the sequence to be amplified. In some embodiments, no more than 95% of nucleic acid fragments in the sample have a length shorter than the length of the sequence to be amplified.

The present application also provides a method of determining a function of a first concentration of a first detected sequence (detected sequence $S_1$) and of a second concentration of a second detected sequence (detected sequence $S_2$) in the same sample of non-fragmented nucleic acids. The function may be a fraction or a ratio.

To this end, the methods described herein may further comprise:

i. measuring the concentration of a second detected sequence in said sample comprising fragmented nucleic acids with a measuring method; and ii. correcting the concentration of said second detected sequence in the fragmented nucleic acids with a correction coefficient to obtain the concentration of said second detected sequence in non-fragmented nucleic acids, wherein the correction coefficient is based on the length distribution (LD) and at least one parameter of the measuring method.

In some embodiments, measuring the concentration of the second detected sequence comprises amplifying a second sequence to be amplified comprising the second detected sequence. In some embodiments, the measuring method comprises a multiplex amplification step. In some embodiments, the length of the first sequence to be amplified is different from the length of the second sequence to be amplified, and a different correction coefficient is applied for the first and second detected sequences. In some embodiments, the length of the first sequence to be amplified and the second sequence to be amplified are the same. In some embodiments, other parameters of the measuring method are different between the first detected sequence and second detected sequence (e.g., parameters related to binding/detection of the probe, or any parameters affecting amplification as described in the "Determining a correction coefficient" sub section below).

In some embodiments, the first sequence to be amplified comprises a mutant allele detected sequence or a variant allele detected sequence and the second sequence to be amplified comprises a corresponding reference allele detected sequence. In some embodiments, the first sequence to be amplified comprises an insertion or deletion compared to a corresponding reference sequence comprised by the second sequence to be amplified. In some embodiments, the method further comprises a step of determining a corrected mutant allele fraction (MAF) of the first detected sequence compared to the second detected sequence. In some embodiments, the method further comprises a step of determining a corrected variant allele fraction (VAF) of the first detected sequence compared to the second detected sequence.

In some embodiments, the first sequence to be amplified is amplified from a variant nucleic acid comprising a copy number variation (CNV) and the second sequence to be amplified is amplified from a reference nucleic acid. In some embodiments, the method further comprises a step of determining a corrected copy number variation ($CNV_{real}$) of the reference sequence compared to the variant sequence.

In any of the preceding embodiments, the method can further comprise a step of calibrating the correction coefficient based on measured concentrations of the detected sequence in a first nucleic acid sample having a first fragment length distribution ($LD_1$) and a second nucleic acid sample having a second fragment length distribution ($LD_2$).

Nucleic Acid Sample and Length Distribution

In some embodiments provided herein, a sample is provided which contains fragmented nucleic acids. The fragmented nucleic acids are actually fragments from original nucleic acids, i.e. non-fragmented nucleic acids, that have undergone fragmentation. Indeed, the concentration of the detected sequence in non-fragmented nucleic acids is the sought-after measure, but the available sample is actually fragmented. In some embodiments, the method does not comprise fragmenting the non-fragmented nucleic acid to generate the sample comprising fragmented nucleic acids.

The sample may contain any type of fragmented nucleic acids. In particular, the sample may be a cell-free sample, i.e. a biologic liquid in which nucleic acids have been released from cells such as saliva, blood plasma, urine or whole blood; or a cell-containing sample, i.e. a biologic sample containing essentially cells, such as a biopsy. Besides, the sample may be a naturally fragmented sample, i.e. the non-fragmented nucleic acids have been degraded naturally before sampling, i.e. in the living organism, or after sampling due to preservation treatments or storage conditions. The sample may finally be an artificially fragmented sample, i.e. non-fragmented nucleic acids are sampled and then degraded artificially for the needs of the measuring method. Further, the sample may be deoxyribonucleic acid (DNA) or ribonucleic acid (RNA).

Examples of cell-free naturally fragmented DNA samples are:

- DNA digested by caspase-activated DNAse during apoptosis and following lysosomal DNAse II digestion after phagocytosis of dying cells; and
- circulating DNA cleaved by plasma nucleases.

Examples of naturally fragmented RNAs samples include but are not limited to messenger RNAs cleaved by ribonucleases (such as endo- and exo-nucleases). These samples may be cell-free or cell-containing samples.

Examples of artificially fragmented DNA and RNA samples are:

- those where nucleic acids are fragmented following formalin fixation followed by embedding in paraffin (FFPE) (an example of a cell-containing sample); and
- those where nucleic acids are fragmented using acoustic shearing methods (an example of a cell-free sample).

The measuring method implemented in the measuring step of the basic method of the invention may be an isothermal quantitative nucleic acid amplification method or a non-isothermal quantitative nucleic acid amplification method.

Isothermal quantitative nucleic acid amplification method may be loop mediated isothermal amplification or quantitative nucleic acid sequence-based amplification. It may be combined with a reverse transcription step to allow the detection of RNA.

Non-isothermal quantitative nucleic acid amplification method may be quantitative Polymerase Chain Reaction, real time Polymerase Chain Reaction, digital Polymerase Chain Reaction, multiplex Polymerase Chain Reaction or multiplex digital Polymerase Chain Reaction. It may be combined with a reverse transcription step to allow the detection of RNA.

In some embodiments of the method, the length distribution (LD) of nucleic acid fragments is provided. In the invention, fragments refer to individual nucleic acids resulting from natural or artificial fragmentation of original non-fragmented nucleic acids. By way of illustration and not limitation, an original non-fragmented nucleic acid with a length of 10000 base pairs (bp) may for example be fragmented in 25 fragments with a length of 75 bp, 50 fragments with a length of 100 bp and 25 fragments with a length of 125 bp, yielding a population of short chain nucleic acids. It is then possible to define a length distribution of nucleic acid fragments in this population, i.e. the number of fragments having a given length, for all possible lengths. Length distribution may be also defined with usual statistical functions (e.g., a Gaussian or Poisson distribution) or parameters like mean value and standard deviation.

Devices suitable to measure length distribution of nucleic acid fragments in a sample are for example the Tape Station 4200 instrument or the Bioanalyzer 2100 instrument, both from Agilent Technologies, or the LabChip GX Touch Nucleic Acid Analyzer from PerkinElmer.

With regards to the length distribution of nucleic acid fragments, fragments with a length shorter than the length of the sequence to be amplified, $L_a$ (or $L_a$−n or $r \cdot L_a$, as described above) will not be replicated. If such fragments contain a part of the sequence to be amplified, it will not be replicated and this leads to an underestimation of the concentration. The methods provided herein can be applied to correct for the resulting underestimation of the concentration of the nucleic acid in the non-fragmented nucleic acid sample.

It is likely that the correction coefficient will be small if only a few fragments have a length shorter than $L_a$ (or $L_a$−n or $r \cdot L_a$). Indeed, applicant notices that the correction coefficient is more relevant when at least 5% of nucleic acid fragments have a length shorter than $L_a$ (or $L_a$−n or $r \cdot L_a$). The proportion of fragments having a length shorter than $L_a$ (or $L_a$−n or $r \cdot L_a$) may be at least 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84% or 85%. In some embodiments, the steps of determining a correction coefficient and correcting the concentration of the detected sequence is applied when at least 5% of nucleic acid fragments have a length shorter than $L_a$ (or $L_a$−n or r·$L_a$).

Besides, it is likely that the correction coefficient will be very high if almost all fragments have a length shorter than $L_a$ (or $L_a$−n or r·$L_a$). Indeed, applicant notices that the correction coefficient is more relevant when at most 95% of nucleic acid fragments have a length shorter than $L_a$ (or $L_a$−n or r·$L_a$). The proportion of fragments having a length shorter than $L_a$ (or $L_a$−n or r·$L_a$) may be at most 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16% or 15%.

In particular, the proportion of fragments having a length shorter than $L_a$ (or $L_a$−n or r·$L_a$) may be in a range selected from 5%-95%, 5%-90%, 5%-85%, 5%-80%, 5%-75%, 5%-70%, 5%-65%, 5%-60%, 5%-55%, 5%-50%, 10%-95%, 10%-90%, 10%-85%, 10%-80%, 10%-75%, 10%-70%, 10%-65%, 10%-60%, 10%-55%, 10%-50%, 15%-95%, 15%-90%, 15%-85%, 15%-80%, 15%-75%, 15%-70%, 15%-65%, 15%-60%, 15%-55%, 15%-50%, 20%-95%, 20%-90%, 20%-85%, 20%-80%, 20%-75%, 20%-70%, 20%-65%, 20%-60%, 20%-55%, 20%-50%, 25%-95%, 25%-90%, 25%-85%, 25%-80%, 25%-75%, 25%-70%, 25%-65%, 25%-60%, 25%-55%, 25%-50%, 30%-95%, 30%-90%, 30%-85%, 30%-80%, 30%-75%, 30%-70%, 30%-65%, 30%-60%, 30%-55%, 30%-50%, 35%-95%, 35%-90%, 35%-85%, 35%-80%, 35%-75%, 35%-70%, 35%-65%, 35%-60%, 35%-55%, 35%-50%, 40%-95%, 40%-90%, 40%-85%, 40%-80%, 40%-75%, 40%-70%, 40%-65%, 40%-60%, 40%-55%, 40%-50%, 45%-95%, 45%-90%, 45%-85%, 45%-80%, 45%-75%, 45%-70%, 45%-65%, 45%-60%, 45%-55%, 45%-50%.

In another embodiment, $L_a$ is longer than 40 bp and shorter than 200 bp, preferably longer than 50 bp and shorter than 170 bp, more preferably longer than 65 bp and shorter than 150 bp, even more preferably longer than 70 bp and shorter than 130 bp. In some embodiments, the length of the sequence to be amplified $L_a$ is in the range 65-70 bp, 70-75 bp, 75-80 bp, 80-90 bp, 90-100 bp, 100-110 bp, 110-120 bp, or 120-130 bp.

In another embodiment, the nucleic acid fragments length distribution is comprised in the range from 10 bp to 1000 bp. The nucleic acid fragments length distribution is preferably comprised in the range from 25 bp to 350 bp, preferably from 30 bp to 320 bp, more preferably from 35 bp to 290 bp, even more preferably from 40 bp to 270 bp.

Determining a Correction Coefficient

In some embodiments, a correction coefficient is determined. Indeed, if an original non-fragmented nucleic acid is fragmented inside the sequence to be amplified, the measuring method used cannot detect that sequence to be amplified. This absence of detection leads to an underestimation of the concentration. This correction coefficient depends on the nucleic acid fragments length distribution, and on parameters relevant to define the probability that a copy of the sequence to be amplified is cut during fragmentation, such as the length of the sequence to be amplified, and potentially on parameters specifically associated to the measuring method.

In some embodiments, the measured concentration of the detected sequence is corrected with the correction coefficient to obtain the concentration of the detected sequence in non-fragmented nucleic acids, i.e. in the original sample.

In some embodiments, the measuring method implemented to measure the concentration of the detected sequence intrinsically uses some parameters relevant to determine the correction coefficient. In some embodiments, the measuring method is an amplification method using replication and an amplification mixture.

A parameter of particular relevance is the length of the sequence to be amplified, hereafter noted $L_a$. The length of the sequence to be amplified $L_a$ is actually the sum of the length of the primers (forward and reverse) plus the length of any additional base pairs located between the primers.

In an embodiment, the length of the sequence to be amplified $L_a$ is equal to or longer than the length of the primers (forward and reverse), and is shorter than 200 bp, preferably shorter than 170 bp, more preferably shorter than 150 bp and even more preferably shorter than 130 bp.

For replication, the primer has first to bind to a nucleic acid. Binding is optimal when all the bases of the primer are complementary to the nucleic acid (for DNA Adenine is complementary to Thymine and Guanine is complementary to Cytosine; for RNA Adenine is complementary to Uracil and Guanine is complementary to Cytosine), but binding may also be efficient if a few bases of the primer are not complementary with the nucleic acid. In other words, if the nucleic acid sequence is shortened by a few bases where the primer should bind, the replication process can still be efficient. A relevant parameter may be $L_a$, or $L_a$−n with n an integer from 1 to 15, or r·$L_a$ (r multiplied by $L_a$) with a shortening coefficient r ranging between 75% and 100% and with the proviso that r·$L_a$ is always an integer value. In some embodiments, r is a value greater than 0.75 and less than 1, greater than 0.8 and less than 1, greater than 0.9 and less than 1, or greater than 0.95 and less than 1, with the proviso that r·$L_a$ is always an integer value.

In some embodiments, a value for n or r can be predicted based on the predicted strength of primer binding to a sequence to be amplified that has been shortened by a few bases where the primers should bind. For example, a value for n or r can be predicted based on parameters of the sequence to be amplified and/or of the primers (e.g., GC content of the sequence to be amplified; GC content of the amplification primers; length of the amplification primers; type of polymerase being used; temperature of the amplification cycles). In some embodiments, a value for n or r can be predicted based on (a) the predicted melting temperatures (Tm) of the primers binding to the full length sequence to be amplified, (b) the predicted melting temperatures of the primers binding to the sequence to be amplified shortened by a factor of n or r as described above (i.e., $L_a$−n or r·$L_a$), and (c) the annealing temperature used in the amplification method.

In some embodiments, a value for n or r can be determined experimentally, e.g. in a calibration step as described in the "Calibrating the correction coefficient" subsection below. In some embodiments, n or r can be determined experimentally for a given sequence to be amplified and set of amplification primers for one sample, and then used to calibrate the L parameter for any sample wherein the sequence to be amplified and amplification conditions are the same.

With the length parameter $L_a$, the correction coefficient may be determined in the following manner.

Let P(X) be the probability of the event X.

Let $L_a$ be the length of the sequence to be amplified (in number of base pairs).

Let f be the probability distribution of the length of nucleic acid fragments in the sample (f(i) is the probability that a fragment in the sample has a length of i base pairs).

Let $$\hat{l} = \sum_{i=1}^{\infty} i f(i)$$

be the average length of the fragments (in number of base pairs).

Let us assume that the cut position of non-fragmented nucleic acids is random and equiprobable along the base pairs.

Let us partition the probability universe Ω in mutually exclusive events:

$$\Omega = \bigcup_{i=1}^{\infty} S(L_a, i)$$

$$\text{Where } S(L_a, i) = \left\{ \begin{matrix} \text{the first base of the sequence to be amplified} \\ \text{belongs to a fragment of length } i \end{matrix} \right\}$$

$$\text{Then } P(\text{sequence to be amplified is not cut}) = \sum_{i=1}^{\infty} \{\text{sequence to be amplified is not cut}\} \cap S(L_a, i)$$

$$\text{By application of Bayes rule } P(A \cap B) = P(A/B)P(B)$$

$$P(\{\text{sequence to be amplified is not cut}\} \cap S(L_a, i)) = P(\{\text{sequence to be amplified is not cut}\}/S(L_a, i))P(S(L_a, i)) \text{ and}$$

$$P(\{\text{sequence to be amplified is not cut}\}/S(L_a, i)) = 1 - P(\{\text{sequence to be amplified is cut}\}/S(L_a, i))$$

$$P(\{\text{sequence to be amplified is not cut}\}/S(L_a, i)) = 1 - \frac{L_a - 1}{i} \text{ if } L_a \le i, \text{ else } 0$$

Besides, let N be the total number of fragments in the fragmented nucleic acid sample:

$$P(S(L_a, i)) = \frac{(Nf(i))i}{\sum_{j=1}^{\infty}(Nf(j))j} \text{ and } P(S(L_a, i)) = \frac{f(i)i}{\sum_{j=1}^{\infty} f(j)j}$$

Thus:

$$P(\text{sequence to be amplified is not cut}) = \sum_{i=1}^{\infty} \{\text{sequence to be amplified is not cut}\} \cap S(L_a, i)P$$

$$(\text{sequence to be amplified is not cut}) = \sum_{i=1}^{\infty} P(\{\text{sequence to be amplified is not cut}\}/S(L_a, i))P(S(L_a, i))$$

$$P(\text{sequence to be amplified is not cut}) = \sum_{i=L_a}^{\infty} \left(1 - \frac{L_a - 1}{i}\right) \frac{f(i)i}{\sum_{j=1}^{\infty} f(j)j}$$

$$\text{And } P(\text{sequence to be amplified is not cut}) = \frac{1}{\hat{l}}\left[\left(\sum_{i=L_a}^{\infty} if(i)\right) + (1 - L_a)\sum_{i=L_a}^{\infty} f(i)\right]$$

Finally, the concentration of the detected sequence in the sample of non-fragmented nucleic acids ($C_{real}$) is obtained after multiplication of the measured concentration of the detected sequence in the sample of fragmented nucleic acids ($C_{measured}$) by a correction factor:

$$C_{real} = C_{measured} \frac{1}{P(\text{sequence to be amplified is not cut})}$$

$$C_{real} = C_{measured} \frac{1}{\frac{1}{\hat{l}}\left[\left(\sum_{i=L_a}^{\infty} if(i)\right) + (1 - L_a)\sum_{i=L_a}^{\infty} f(i)\right]}$$

This correction factor depends on the length distribution of nucleic acid fragments in the sample (f) and on a parameter of the amplification method, namely the length of the sequence to be amplified $L_a$.

The correction coefficient may be computed similarly with a $L_a$–n with n being an integer greater than 0 (e.g., an integer from 1 to 15, 1 to 10, or 1 to 5) or $r \cdot L_a$ (r multiplied by $L_a$) with a shortening coefficient r ranging between 75% and 100% and with the proviso that $r \cdot L_a$ is always an integer value to take into account shortened fragments still leading to replication.

For example, in some embodiments wherein a set of amplification primers can still bind to and amplify a target region shortened by a factor of n, the correction coefficient is determined by:

$$\frac{1}{\frac{1}{\hat{l}}[(\Sigma_{i=L}^{\infty} if(i)) + (1 - L)\Sigma_{i=L}^{\infty} f(i)]};$$

wherein L is the length of the target region minus n ($L_a$–n), wherein n is an integer from 1 to 15;

wherein f(i) is the probability that a fragment in the sample has a length of i base pairs; and wherein $$\hat{l} = \sum_{i=1}^{\infty} i f(i)$$

is the average length of the nucleic acid fragments.

In some embodiments wherein a set of amplification primers can still bind to and amplify a target region shortened by a shortening coefficient r, the correction coefficient is determined by:

$$\frac{1}{\frac{1}{\hat{l}}[(\Sigma_{i=L}^{\infty} if(i)) + (1 - L)\Sigma_{i=L}^{\infty} f(i)]};$$

wherein L is the length of the target region multiplied by r ($r \cdot L_a$), wherein r is at least 0.75 and less than 1, with the proviso that $r \cdot L_a$ is always an integer value;

wherein f(0 is the probability that a fragment in the sample has a length of i base pairs; and wherein $$\hat{l} = \sum_{i=1}^{\infty} i f(i)$$

is the average length of the nucleic acid fragments.

Notably, it may be relevant in some cases to measure the fraction of a nucleic acid that has undergone a mutation, for instance a mutant allelic fraction (MAF). In this particular case, the first detected sequence ($S_1$) is the mutant (mut) and the second detected sequence ($S_2$) is the wild-type (wt). When both detected sequences are associated with sequences to be amplified of different lengths, the correction coefficients for both concentrations are different and must be considered.

It may be also relevant in some cases to measure the ratio of a variant nucleic acid (var) that has been amplified with regards to a reference nucleic acid (ref) that has been amplified (the variant being not necessarily a mutation of reference), namely a copy number variation (CNV).

In some embodiments, this method comprises the following steps.

In a first step, the concentration of $S_1$ in non-fragmented nucleic acids is determined according to the basic method described above. In this step, the correction coefficient is determined with consideration of the length of the sequence to be amplified associated with $S_1$.

In a second step, the concentration of $S_2$ in non-fragmented nucleic acids is determined according to the basic method described above. In this step, the correction coefficient is determined with consideration of the length of the sequence to be amplified associated with $S_2$.

In a third step, the function of the $S_1$ concentration and of the $S_2$ concentration is determined.

In this method said $S_1$ concentration and said $S_2$ concentration are determined in the same sample. To perform the measurements of the $S_1$ and $S_2$ concentrations on the same sample, multiplex PCR or multiplex digital PCR is particularly suitable.

In this method, the length of the sequence to be amplified associated with $S_1$ is different from the length of the sequence to be amplified associated with $S_2$.

For the specific case of a mutant allelic fraction (MAF), the function is a fraction determined with following relation:

$$MAF_{measured} = \frac{1}{1 + \frac{C_{measured}(wt)}{C_{measured}(mut)}}$$

$$MAF_{real} = \frac{1}{1 + \left(\frac{1}{MAF_{measured}} - 1\right)\frac{\left(\Sigma_{i=L_{a(mut)}}^{\infty} if(i)\right) + (1 - L_{a(mut)})\Sigma_{i=L_{a(mut)}}^{\infty} f(i)}{\left(\Sigma_{i=L_{a(wt)}}^{\infty} if(i)\right) + (1 - L_{a(wt)})\Sigma_{i=L_{a(wt)}}^{\infty} f(i)}}$$

A corrected variant allelic fraction (VAF) can be determined according to the same method used to determine a mutant allelic fraction (MAF).

For the specific case of a copy number variation (CNV), the function is a ratio determined with following relation:

$$CNV_{measured} = \frac{C_{measured}(\text{var})}{C_{measured}(ref)}$$

$$CNV_{real} = CNV_{measured}\frac{\left(\Sigma_{i=L_{a(ref)}}^{\infty} if(i)\right) + (1 - L_{a(ref)})\Sigma_{i=L_{a(ref)}}^{\infty} f(i)}{\left(\Sigma_{i=L_{a(var)}}^{\infty} if(i)\right) + (1 - L_{a(var)})\Sigma_{i=L_{a(var)}}^{\infty} f(i)}$$

Calibrating the Correction Coefficient

In some embodiments the method further comprises a step of calibrating the correction coefficient. In some embodiments, the calibration coefficient is calibrated based on parameters of the sequence to be amplified or parameters of the measuring method (e.g., parameters of the amplification or detection steps).

In some embodiments provided herein, the correction coefficient can also be based on the probability that the sequence to be amplified is fragmented based on sequence fragmentation bias. In some embodiments, the relative probability that a sequence to be amplified will be fragmented is known. In some embodiments, the probability that the sequence to be amplified will be fragmented depends on the source of fragmentation (e.g., naturally-occurring nucleic acid fragmentation or fragmentation by physical means such as sonication). In some embodiments, the fragmentation bias depends on the chromatin structure of the region comprising the sequence to be amplified.

In some embodiments, the fragmentation bias depends on the relative occurrence of sequence associated with fragmentation within the sequence to be amplified (e.g., a site targeted by a restriction enzyme).

For example, in some embodiments, the nucleic acid sample can comprise DNA digested by caspase-activated DNAse during apoptosis. In some embodiments, the correction coefficient can comprise a correction factor based on the probability that the sequence to be amplified is fragmented during apoptosis. In the majority of somatic tissues, apoptotic cleavage of DNA results in the formation of fragments roughly 195 bp. in length and multiples thereof, whereas the fragmentation pattern of the neuronal chromatin is characterized by size of ~165 bp. The repeatable length corresponds to single nucleosome size (with degraded DNA linkers). Within the nucleosomal core, DNA is protected from nucleases by histones, whereas the linker is vulnerable to digestion. Thus, in some embodiments a correction factor is applied to the correction coefficient that represents the probability the sequence to be amplified is fragmented based on its positioning in a chromatin structure (e.g., in a nucleosome or linker region).

In some embodiments, sequence fragmentation bias is a positional bias. For example, in some embodiments the nucleic acid sample is an RNA sample. RNA transcripts may be preferentially cut at certain positions within the transcript, e.g. at the start and/or at the end of the transcript. (Tuerk A, Wiktorin G, Güler S (2017) *Mixture models reveal multiple positional bias types in RNA-Seq data and lead to accurate transcript concentration estimates.* PLOS Computational Biology 13(5): e1005515). Hence, this type of bias is referred to as positional bias. Thus, in some embodiments a correction factor is applied to the correction coefficient that represents the probability the sequence to be amplified is fragmented based on the position of the sequence to be amplified within an RNA transcript.

In some embodiments, the nucleic acid sample can comprise artificially fragmented nucleic acids, e.g., nucleic acids produced by mechanical shearing or enzymatic fragmentation. For nucleic acid samples comprising enzymatically fragmented nucleic acids, a correction factor can be applied to the correction coefficient that accounts for the recognition sequences or sequence preferences of the enzymes used (e.g., sequence bias of a transposase).

In some embodiments, the at least one parameter of the measuring method can further comprise a parameter of the amplifying step selected from the group consisting of: GC content of the sequence to be amplified; GC content of the amplification primers; length of the amplification primers; type of polymerase being used; and temperature of the amplification cycles. In some embodiments, the at least one parameter of the measuring method can further comprise a parameter of the measuring step selected from the group consisting of: sequence of a detecting probe; photostability of a fluorophore used; chemical stability of a fluorophore used; quantum yield of a fluorophore used; and wavelength of a fluorophore used. In some embodiments, the additional parameter of the amplifying step can be incorporated as a coefficient multiplied by the length distribution (LD) curve, or as a calibration coefficient multiplied by the correction coefficient.

In some embodiments, the effect of the additional parameters of the measuring method as described above can be determined experimentally and incorporated into the correction coefficient as an experimentally determined calibration factor.

In some embodiments the method further comprises a step of calibrating the correction coefficient based on measured concentrations of the detected sequence in a first nucleic acid sample having a first fragment length distribution ($LD_1$) and a second nucleic acid sample having a second fragment length distribution ($LD_2$). In some embodiments, the first nucleic acid sample is a non-fragmented sample. In some embodiments, the first nucleic acid sample comprises fragmented nucleic acids wherein less than 5% of the nucleic acid fragments have a length shorter than the length of the sequence to be amplified. In some embodiments, the first nucleic acid sample is used to determine a ground-truth correction factor for the second nucleic acid sample. The relative error between the ground-truth correction factor and the predicted correction coefficient can be determined, and applied to the calculation of a corrected concentration of the detected sequence as a calibration factor.

In some embodiments, n or r can be determined based on what value of n or r yields the best fit between the predicted correction coefficient and the ground-truth correction factor, as one skilled in the art would readily understand.

In some methods according to any one of the embodiments provided herein, the method further comprises correcting the concentration with a calibration factor based on any one of the parameters described above. In some embodiments, the calibration factor can be applied as a modified dilution factor according to any one of the measuring methods provided herein.

II. SYSTEMS OF THE PRESENT APPLICATION

Last, the invention relates to a system configured to determine the concentration of a detected sequence in non-fragmented nucleic acids. This system comprises the following modules.

A first a module is configured to measure the concentration of the detected sequence in a sample of fragmented nucleic acids, said fragmented nucleic acids being derived from said non-fragmented nucleic acids. This module realizes the measuring step of the basic method of the invention.

A suitable module comprises a real-time thermocycler and uses a reaction mixture including primers, intercalating fluorescent dye or fluorescent probes and polymerase enzyme in an appropriate buffer to perform the amplification reaction. Alternatively, a digital PCR platform may be used in place of a real-time thermocycler. Such a digital PCR platform is composed of a PCR reservoir (often a tube, plate or microfluidic chip) a partitioning system, a thermocycler and a fluorescence reader together with analysis software.

A second module is configured to compute a correction coefficient depending on the nucleic acid fragments length distribution of said fragmented nucleic acids and on parameters of said measure. This module is typically a computer device comprising a display screen, at least one microprocessor, a data exchange module and at least one computer-readable storage medium. Alternatively, this module may be connected to a remote server comprising at least one microprocessor, a data exchange module and at least one computer-readable storage medium.

A computer program comprising instructions which, when the program is executed by the computer or remote server, may cause the computer or remote server to automatically compute the correction coefficient.

A computer-readable storage medium comprising instructions which, when the program is executed by the computer or remote server, may be used. In an embodiment, the computer-readable storage medium is a non-transitory computer-readable storage medium.

A third module is configured to compute the concentration of the detected sequence in non-fragmented nucleic acids with the correction coefficient.

The first module may be an isothermal quantitative nucleic acid amplification module or a non-isothermal quantitative nucleic acid amplification module.

Isothermal quantitative nucleic acid amplification module typically comprises primers, intercalating fluorescent dye and a polymerase enzyme compatible with isothermal amplification in an appropriate isothermal buffer to perform the amplification reaction and a thermo-regulated fluorescent scanner equipped with compatible analysis software. Suitable modules are modules performing loop-mediated isothermal amplification, quantitative nucleic acid sequence-based amplification, signal-mediated amplification of RNA technology and strand displacement amplification.

Non-isothermal quantitative nucleic acid amplification module is typically quantitative Polymerase Chain Reaction module, real time Polymerase Chain Reaction module, digital Polymerase Chain Reaction module, multiplex Polymerase Chain Reaction module and multiplex digital Polymerase Chain Reaction module.

The second module may use the length of the sequence to be amplified as a parameter of the measure performed by the first module to compute the correction coefficient.

All these parameters may be included one by one or in combinations in the computation of the correction coefficient done by second module.

III. EXEMPLARY EMBODIMENTS

An aspect of the present application provides methods of correcting the concentration of a detected sequence in non-fragmented nucleic acids. Another aspect of present application provides systems configured to determine the concentration of a detected sequence in non-fragmented nucleic acids.

To this end, the present application provides the following exemplary embodiments:

Embodiment 1. A method of determining the concentration of a detected sequence in non-fragmented nucleic acids comprising the following steps:

i. providing a sample of fragmented nucleic acids, said fragmented nucleic acids being derived from said non-fragmented nucleic acids;

ii. providing the nucleic acid fragments length distribution (LD) of said fragmented nucleic acids;
iii. measuring the concentration of said detected sequence in said sample of fragmented nucleic acids with a measuring method;
iv. determining a correction coefficient depending on said nucleic acid fragments length distribution (LD) of said fragmented nucleic acids and on parameters of said measuring method; and
v. correcting the concentration of said detected sequence in the fragmented nucleic acids with said correction coefficient to obtain the concentration of said detected sequence in non-fragmented nucleic acids.

Embodiment 2. The method of determining the concentration of a detected sequence in non-fragmented nucleic acids according to embodiment 1, wherein the sample of fragmented nucleic acids is any combination of the following three categories:
i. either a cell-free sample or a cell-containing sample;
ii. either a naturally fragmented sample or an artificially fragmented sample; and
iii. any type of deoxyribonucleic acid or ribonucleic acid.

Embodiment 3. The method of determining the concentration of a detected sequence in non-fragmented nucleic acids according to any of the preceding embodiments, wherein said measuring method is an isothermal quantitative nucleic acid amplification method, preferably selected from loop-mediated isothermal amplification and quantitative nucleic acid sequence-based amplification.

Embodiment 4. The method of determining the concentration of a detected sequence in non-fragmented nucleic acids according to embodiment 1 or 2, wherein said measuring method is a non-isothermal quantitative nucleic acid amplification method, preferably selected from quantitative Polymerase Chain Reaction, real time Polymerase Chain Reaction, digital Polymerase Chain Reaction, multiplex Polymerase Chain Reaction and multiplex digital Polymerase Chain Reaction.

Embodiment 5. The method of determining the concentration of a detected sequence in non-fragmented nucleic acids according to embodiment 3 or 4, wherein the parameters of said measuring method include length of the sequence to be amplified.

Embodiment 6. The method of determining the concentration of a detected sequence in non-fragmented nucleic acids according to embodiment 5, wherein at least 5% of nucleic acid fragments have a length shorter than the length of the sequence to be amplified.

Embodiment 7. The method of determining the concentration of a detected sequence in non-fragmented nucleic acids according to embodiment 5 or 6, wherein at most 95% of nucleic acid fragments have a length shorter than the length of the sequence to be amplified.

Embodiment 8. The method of determining the concentration of a detected sequence in non-fragmented nucleic acids according to any one of embodiments 5 to 7, wherein the length of the sequence to be amplified is longer than 40 bp and shorter than 200 bp, preferably longer than 50 bp and shorter than 170 bp, more preferably longer than 65 bp and shorter than 150 bp, even more preferably longer than 70 bp and shorter than 130 bp.

Embodiment 9. The method of determining the concentration of a detected sequence in non-fragmented nucleic acids according to any one of embodiments 1 to 8, wherein the nucleic acid fragments length distribution is comprised in the range of from 25 bp to 350 bp, preferably from 30 bp to 320 bp, more preferably from 35 bp to 290 bp, even more preferably from 40 bp to 270 bp.

Embodiment 10. A method of determining a function of a first concentration of a first detected sequence $S_1$ and of a second concentration of a second detected sequence $S_2$ in non-fragmented nucleic acids comprising
iv. determining the concentration of $S_1$ in said non-fragmented nucleic acids according to any one of embodiments 5 to 9;
v. determining the concentration of $S_2$ in said non-fragmented nucleic acids according to any one of embodiments 5 to 9; and
vi. computing said function of said $S_1$ concentration and said $S_2$ concentration;
wherein said $S_1$ concentration and said $S_2$ concentration are determined in the same sample; and
wherein the length of the sequence to be amplified associated with $S_1$ is different from the length of the sequence to be amplified associated with $S_2$.

Embodiment 11. A system configured to determine the concentration of a detected sequence in non-fragmented nucleic acids comprising
i. a module configured to measure the concentration of said detected sequence in a sample of fragmented nucleic acids, said fragmented nucleic acids being derived from said non-fragmented nucleic acids;
ii. a module configured to compute a correction coefficient depending on the nucleic acid fragments length distribution (LD) of said fragmented nucleic acids and on parameters of said measure; and
iii. a module configured to compute the concentration of said detected sequence in non-fragmented nucleic acids with said correction coefficient.

Embodiment 12. A system configured to determine the concentration of a detected sequence in non-fragmented nucleic acids according to embodiment 11, wherein the module configured to measure the concentration of said detected sequence in said fragmented nucleic acids is an isothermal quantitative nucleic acid amplification module, preferably selected from loop mediated isothermal amplification module and quantitative nucleic acid sequence-based amplification module.

Embodiment 13. A system configured to determine the concentration of a detected sequence in non-fragmented nucleic acids according to embodiment 11, wherein the module configured to measure the concentration of said detected sequence in said fragmented nucleic acids is a non-isothermal quantitative nucleic acid amplification module, preferably selected from quantitative Polymerase Chain Reaction module, real time Polymerase Chain Reaction module, digital Polymerase Chain Reaction module, multiplex Polymerase Chain Reaction module and multiplex digital Polymerase Chain Reaction.

Embodiment 14. A system configured to determine the concentration of a detected sequence in non-fragmented nucleic acids according to embodiment 12 or 13, wherein the parameters of said measure include the length of the sequence to be amplified.

IV. EMBODIMENTS

An aspect of the present application provides methods of correcting for problems related to underestimation of the presence of the nucleic acid sequence of interest in a nucleic acid sample comprising fragmented nucleic acids. Another aspect of present application provides systems configured to determine the concentration of a detected sequence in non-fragmented nucleic acids.

To this end, the present application provides embodiments as follows:

Embodiment 1'. A method of determining the concentration of a detected sequence in non-fragmented nucleic acids comprising the following steps:

i. determining a length distribution of nucleic acids in a sample comprising fragmented nucleic acids, wherein the fragmented nucleic acids are derived from said non-fragmented nucleic acids;

ii. measuring the concentration of said detected sequence in said sample comprising fragmented nucleic acids with a measuring method;

and iii. correcting the measured concentration of said detected sequence in the sample comprising fragmented nucleic acids with a correction coefficient to obtain the concentration of said detected sequence in non-fragmented nucleic acids, wherein the correction coefficient is based on the length distribution and at least one parameter of the measuring method.

Embodiment 2'. The method of embodiment 1', wherein measuring the concentration of the detected sequence comprises amplifying a sequence to be amplified comprising the detected sequence.

Embodiment 3'. The method of embodiment 2', wherein the detected sequence and the sequence to be amplified are the same, and wherein the step of measuring comprises detecting incorporation of a label in nucleic acids produced during amplification.

Embodiment 4'. The method of embodiment 3', wherein the label is a fluorescent dye comprising a fluorophore.

Embodiment 5'. The method of embodiment 2', wherein the detected sequence is a subset of the sequence to be amplified, and wherein the step of measuring comprises detecting binding of a labeled probe to the detected sequence.

Embodiment 6'. The method of embodiment 4', wherein the labeled probe is a fluorescently labeled probe comprising a fluorophore.

Embodiment 7'. The method of any one of the preceding embodiments, wherein the method further comprises a step of determining the correction coefficient based on the length distribution (LD) of nucleic acids in the sample and at least one parameter of said measuring method.

Embodiment 8'. The method of any one of the preceding embodiments, wherein the at least one parameter of the measuring method comprises length of the sequence to be amplified ($L_a$).

Embodiment 9'. The method of any of embodiments 2'-8', wherein the correction coefficient is determined by:

$$\frac{1}{\frac{1}{\hat{l}}[(\Sigma_{i=L}^{\infty} i f(i)) + (1-L)\Sigma_{i=L}^{\infty} f(i)]};$$

wherein L is the length of the sequence to be amplified ($L_a$);

wherein f(i) is the probability that a fragment in the sample has a length of i base pairs; and wherein $$\hat{l} = \sum_{i=1}^{\infty} \text{i}f(i)$$

is the average length of the nucleic acid fragments.

Embodiment 10'. The method of any one of embodiments 2'-8', wherein a set of amplification primers can still bind to a sequence to be amplified shortened by a factor of n, and wherein the correction coefficient is determined by:

$$\frac{1}{\frac{1}{\hat{l}}[(\Sigma_{i=L}^{\infty} i f(i)) + (1-L)\Sigma_{i=L}^{\infty} f(i)]};$$

wherein L is the length of the sequence to be amplified minus n ($L_a$–n), wherein n is an integer from 1 to 15;

wherein f(i) is the probability that a fragment in the sample has a length of i base pairs; and wherein $$\hat{l} = \sum_{i=1}^{\infty} \text{i}f(i)$$

is the average length of the nucleic acid fragments.

Embodiment 11'. The method of embodiment 10', wherein n is an integer from 1 to 5.

Embodiment 12'. The method of any of embodiments 2'-8', wherein a set of amplification primers can still bind to a sequence to be amplified shortened by a shortening coefficient r, and wherein the correction coefficient is determined by:

$$\frac{1}{\frac{1}{\hat{l}}[(\Sigma_{i=L}^{\infty} i f(i)) + (1-L)\Sigma_{i=L}^{\infty} f(i)]};$$

wherein L is the length of the sequence to be amplified multiplied by r wherein r is at least 0.75 and less than 1, with the proviso that $r \cdot L_a$ is always an integer value;

wherein f(i) is the probability that a fragment in the sample has a length of i base pairs; and wherein $$\hat{l} = \sum_{i=1}^{\infty} \text{i}f(i)$$

is the average length of the nucleic acid fragments.

Embodiment 13'. The method of any one of the preceding embodiments, wherein the correction coefficient is also based on the probability that the sequence to be amplified is fragmented based on sequence fragmentation bias.

Embodiment 14'. The method of any of embodiments 2'-13', wherein the at least one parameter of the measuring method further comprises a parameter of the amplifying step selected from the group consisting of: GC content of the sequence to be amplified; GC content of the amplification primers; length of the amplification primers; type of polymerase being used; temperature of the amplification cycles.

Embodiment 15'. The method of any one of embodiments 4' or 6', wherein the at least one parameter of the measuring method further comprises a parameter of the measuring step selected from the group consisting of: sequence of a detecting probe; photostability of a fluorophore used; chemical stability of a fluorophore used; quantum yield of a fluorophore used; and wavelength of a fluorophore used.

Embodiment 16'. The method of any one of the preceding embodiments, wherein the correcting comprises multiplying the concentration measured in the sample comprising fragmented nucleic acids with the correction coefficient.

Embodiment 17'. The method of any one of the preceding embodiments, wherein the correcting is applied if at least 5% of the nucleic acids in the sample have a length shorter than the length of the sequence to be amplified.

Embodiment 18'. The method of any one of the preceding embodiments, wherein no more than 95% of nucleic acid fragments in the sample have a length shorter than the length of the sequence to be amplified.

Embodiment 19'. The method of any one of the preceding embodiments, wherein the length of the sequence to be amplified is longer than 40 bp and shorter than 200 bp.

Embodiment 20'. The method of embodiment 19', wherein the length of the sequence to be amplified is longer than 50 bp and shorter than 170 bp.

Embodiment 21'. The method of embodiment 19', wherein the length of the sequence to be amplified is longer than 65 bp and shorter than 150 bp.

Embodiment 22'. The method of embodiment 19', wherein the length of the sequence to be amplified is longer than 70 bp and shorter than 130 bp.

Embodiment 23'. The method of any one of the preceding embodiments, wherein the length distribution (LD) of nucleic acid fragments in the sample is comprised in a range of from 25 bp to 350 bp.

Embodiment 24'. The method of embodiment 23', wherein the length distribution (LD) of nucleic acid fragments in the sample is comprised in a range of from 30 bp to 320 bp.

Embodiment 25'. The method of embodiment 23', wherein the length distribution (LD) of nucleic acid fragments in the sample is comprised in a range of from 35 bp to 290 bp.

Embodiment 26'. The method of embodiment 23', wherein the length distribution (LD) of nucleic acid fragments in the sample is comprised in a range of from 40 bp to 270 bp.

Embodiment 27'. The method of any one of the preceding embodiments, wherein the method does not comprise obtaining the sequence of the fragmented nucleic acids.

Embodiment 28'. The method of any one of the preceding embodiments, wherein the method does not comprise obtaining or predicting the genetic coordinates of the fragmented nucleic acids.

Embodiment 29'. The method of any one of the preceding embodiments, wherein the method does not comprise assembly of the fragmented nucleic acids into a contiguous sequence.

Embodiment 30'. The method of any one of the preceding embodiments, wherein the method does not comprise fragmenting the non-fragmented nucleic acid to generate the sample comprising fragmented nucleic acids.

Embodiment 31'. The method of any one of the preceding embodiments, wherein the measuring method does not comprise sequencing the nucleic acids in the sample.

Embodiment 32'. The method of any one of the preceding embodiments, wherein the sample comprising fragmented nucleic acids is a cell-containing sample.

Embodiment 33'. The method of any one of embodiments 1'-31', wherein the sample comprising fragmented nucleic acids is a cell-free sample.

Embodiment 34'. The method of any one of the preceding embodiments, wherein the sample comprising fragmented nucleic acids is a naturally fragmented sample.

Embodiment 35'. The method of any one of embodiments 1'-29' or 31'-33', wherein the sample comprising fragmented nucleic acids is an artificially fragmented sample.

Embodiment 36'. The method of any one of the preceding embodiments, wherein the sample comprising fragmented nucleic acids is a deoxyribonucleic acid sample.

Embodiment 37'. The method of any one of the preceding embodiments, wherein the sample comprising fragmented nucleic acids is a ribonucleic acid sample.

Embodiment 38'. The method of determining the concentration of a detected sequence in non-fragmented nucleic acids according to any one of the embodiments 2'-37', wherein said measuring method is an isothermal quantitative nucleic acid amplification method.

Embodiment 39'. The method of embodiment 38', wherein the measuring method is selected from the group consisting of loop-mediated isothermal amplification and quantitative nucleic acid sequence-based amplification.

Embodiment 40'. The method of any one of embodiments 2'-37', wherein the measuring method is a non-isothermal quantitative nucleic acid amplification method.

Embodiment 41'. The method of embodiment 40', wherein the measuring method is selected from the group consisting of quantitative Polymerase Chain Reaction, real time Polymerase Chain Reaction, digital Polymerase Chain Reaction, multiplex Polymerase Chain Reaction and multiplex digital Polymerase Chain Reaction.

Embodiment 42'. The method of any one of the preceding embodiments, wherein the method further comprises a step of calibrating the correction coefficient based on measured concentrations of the detected sequence in a first nucleic acid sample having a first fragment length distribution ($LD_1$) and a second nucleic acid sample having a second fragment length distribution ($LD_2$).

Embodiment 43'. The method of any one of the preceding embodiments, wherein the method further comprises:

i. measuring the concentration of a second detected sequence in said sample comprising fragmented nucleic acids with a measuring method; and ii. correcting the measured concentration of said second detected sequence in the fragmented nucleic acids with a correction coefficient to obtain the concentration of said second detected sequence in non-fragmented nucleic acids, wherein the correction coefficient is based on the length distribution (LD) and at least one parameter of the measuring method.

Embodiment 44'. The method of embodiment 43', wherein measuring the concentration of the second detected sequence comprises amplifying a second sequence to be amplified comprising the second detected sequence.

Embodiment 45'. The method of embodiment 44', wherein the length of the first sequence to be amplified is different from the length of the second sequence to be amplified.

Embodiment 46'. The method of any of embodiments 43'-45', wherein the first sequence to be amplified comprises a mutant allele detected sequence and the second sequence to be amplified comprises a corresponding reference allele detected sequence.

Embodiment 47'. The method of any of embodiments 43'-45', wherein the first sequence to be amplified comprises an insertion or deletion compared to a corresponding reference sequence comprised by the second sequence to be amplified.

Embodiment 48'. The method of any of embodiments 43'-45', wherein the method further comprises a step of determining a corrected mutant allele fraction (MAF) of the first detected sequence compared to the second detected sequence.

Embodiment 49'. The method of embodiment 48', wherein the corrected MAF ($MAF_{real}$) is calculated using:

$$MAF_{real} = \frac{1}{1+\left(\frac{1}{MAF_{measured}}-1\right)\frac{\left(\Sigma_{i=L_{a(mut)}}^{\infty} if(i)\right)+(1-L_{a(mut)})\Sigma_{i=L_{a(mut)}}^{\infty} f(i)}{\left(\Sigma_{i=L_{a(wt)}}^{\infty} if(i)\right)+(1-L_{a(wt)})\Sigma_{i=L_{a(wt)}}^{\infty} f(i)}}$$

Embodiment 50'. The method of any of embodiments 43'-45', wherein the first sequence to be amplified is amplified from a variant nucleic acid comprising a copy number variation (CNV) and the second sequence to be amplified is amplified from a reference nucleic acid.

Embodiment 51'. The method of any of embodiments 43'-45', wherein the first sequence to be amplified is amplified from a variant nucleic acid comprising a copy number variation (CNV) and the second sequence to be amplified is amplified from a reference nucleic acid.

Embodiment 52'. The method of any of embodiments 43'-45', wherein the first sequence to be amplified is amplified from a variant nucleic acid comprising a copy number variation (CNV) and the second sequence to be amplified is amplified from a reference nucleic acid.

Embodiment 53'. The method of embodiment 50', wherein the method further comprises a step of determining a corrected copy number variation ($CNV_{real}$) of the reference sequence compared to the variant sequence, using the formula:

$$CNV_{real} = CNV_{measured}\frac{\left(\Sigma_{i=L_{a(ref)}}^{\infty} if(i)\right)+(1-L_{a(ref)})\Sigma_{i=L_{a(ref)}}^{\infty} f(i)}{\left(\Sigma_{i=L_{a(var)}}^{\infty} if(i)\right)+(1-L_{a(var)})\Sigma_{i=L_{a(var)}}^{\infty} f(i)}$$

Embodiment 54'. The method of any one of embodiments 43'-51' wherein the measuring method comprises a multiplex amplification step.

Embodiment 55'. A system configured to determine the concentration of a detected sequence in non-fragmented nucleic acids comprising i. a module configured to measure the concentration of said detected sequence in a sample comprising fragmented nucleic acids, said fragmented nucleic acids being derived from said non-fragmented nucleic acids;

ii. a module configured to compute a correction coefficient depending on a length distribution (LD) of nucleic acids in the sample and on parameters of said measure; and iii. a module configured to compute the concentration of said detected sequence in non-fragmented nucleic acids with said correction coefficient.

Embodiment 56'. The system configured to determine the concentration of a detected sequence in non-fragmented nucleic acids according to embodiment 53', wherein the module configured to measure the concentration of said detected sequence in said fragmented nucleic acids is an isothermal quantitative nucleic acid amplification module, selected from loop mediated isothermal amplification module and quantitative nucleic acid sequence-based amplification module.

Embodiment 57'. The system configured to determine the concentration of a detected sequence in non-fragmented nucleic acids according to embodiment 53', wherein the module configured to measure the concentration of said detected sequence in said fragmented nucleic acids is a non-isothermal quantitative nucleic acid amplification module, selected from quantitative Polymerase Chain Reaction module, real time Polymerase Chain Reaction module, digital Polymerase Chain Reaction module, multiplex Polymerase Chain Reaction module and multiplex digital Polymerase Chain Reaction.

Embodiment 58'. The system configured to determine the concentration of a detected sequence in non-fragmented nucleic acids according to embodiment 54' or 55, wherein the parameters of said measure include the length of the sequence to be amplified.

Embodiment 59'. A method of determining a copy number variation (CNV) of a first concentration of a first detected sequence $S_1$ and of a second concentration of a second detected sequence $S_2$ in non-fragmented nucleic acids, comprising:

i. measuring the concentrations of $S_1$ and $S_2$ in a nucleic acid sample comprising fragmented nucleic acids, ii. correcting the measured concentrations of $S_1$ and $S_2$ in the sample comprising fragmented nucleic acids with a correction coefficient to obtain the concentration of said detected sequence in non-fragmented nucleic acids, wherein the correction coefficient is based on the length distribution (LD) and at least one parameter of the measuring method;

iii. computing the CNV using the corrected concentrations of $S_1$ and $S_2$;

wherein the concentrations of $S_1$ and $S_2$ are measured in the same sample; and wherein the at least one parameter of the measuring method associated with $S_1$ is different from the at least one parameter of the measuring method associated with $S_2$.

Embodiment 60'. The method of embodiment 59', wherein measuring the concentrations of $S_1$ and $S_2$ comprises amplifying a first sequence to be amplified comprising $S_1$ and a second sequence to be amplified comprising $S_2$.

Embodiment 61'. The method of embodiment 60', wherein the at least one parameter of the measuring method comprises length of the sequence to be amplified.

Embodiment 62'. The method of embodiment 61', wherein the length of the sequence to be amplified comprising $S_1$ is different from the length of the sequence to be amplified comprising $S_2$.

While various embodiments have been described and illustrated, the detailed description is not to be construed as being limited hereto. Various modifications can be made to the embodiments by those skilled in the art without departing from the true spirit and scope of the disclosure as defined by the claims.

Example 1

Methods for Example 1 a. Preparation of Sonicated DNA

The starting sample is a 200 ng/μl of stock DNA (=6.06E+4 cp/μl) (Human Genomic DNA, Bio-35025, Bioline, Paris, France) with an average length greater than 50 kbp according to the manufacturer.

The Covaris® microtube-15 is used (with 15 to 20 μl±1), which can contain up to 1 μg of DNA according to the manufacturer. Therefore, a dilution step of the stock solution of DNA is performed with TE: Tris-EDTA. This results in a DNA solution of 60 ng/μ0.1 (=1.82E+4 cp/μl), which can be sonicated in the Covaris® microtube-15.

Sonication is performed on a M220 Focused-ultrasonicator (Covaris®, Brighton, United Kingdom).

Firstly, the smallest fragment achievable by Covaris® (length distribution centered around 150 bp) is prepared in order to get as close as possible to the distribution of human DNA fragment lengths, i.e. close to the modes (163, 316 and 465 bp) found in human plasma.

Subsequently, length distributions centered around 200 bp, 350 bp and 550 bp are prepared.

All sonications were made in Covaris® microtube-50 (55 μl±2.5) or microtube Snap-Cap (130 μl±5) which can contain up to 5 μg of DNA according to the manufacturer.

b. Verification of Sonicated DNA Samples with TapeStation

Grayscale data is extracted from the 4200 TapeStation system (Agilent Technologies, Santa Clara, California, USA) electrophoresis images in order to get the base pair distribution required to calculate all the theoretical correction factors. In order to convert mass units into base pair units, the image intensity was inverted and then divided by the fragment length expected at the image pixel location.

High Sensitivity D1000 ScreenTape is used.

c. Primers, Probes and Fluorophores

Primers and probes used were synthesized by Eurogentec (Eurogentec, Angers, France) and purified by high performance liquid chromatography (HPLC) in reverse phase.

The fluorophores used in the TriPlex PCR experiments are: FAM, HEX, and Cyanine (Cy5) as follows:

FAM fluorophore in the Blue Channel to detect the sequence BRAF V600 WT using a sequence to be amplified of length 117 base pairs;

HEX fluorophore in the Green Channel to detect the sequence EGFR L858 WT using a sequence to be amplified of length 78 base pairs;

Cy5 fluorophore in the Red Channel to detect the sequence ALB using a sequence to be amplified of length 81 base pairs.

Preparation template BRAF-EGFR-ALB is shown in Table 1. The notation means Locked Nucleic Acid base.

TABLE 1

| Detected sequence | Primers & probes | Initial concentration (μM) | Final concentration (μM) | 5' to 3' sequence | SEQ ID NOs |
|---|---|---|---|---|---|
| BRAF | Primer Forward | 200 | 0.5 | TACTGTTTTCCTTTACTTACTACACCTCAG | 1 |
| V600 | Primer Reverse | 200 | 0.5 | ACTGATGGGACCCACTCCATC | 2 |
| WT | Probe (FAM) | 100 | 0.25 | CTAGCTACA{G}{T}GAAATCTCG | 3 |
| EGFR | Primer Forward | 200 | 0.5 | GCAGCATGTCAAGATCACAGATT | 4 |
| L858 | Primer Reverse | 200 | 0.5 | CCTCCTTCTGCATGGTATTCTTTCT | 5 |
| WT | Probe (HEX) | 200 | 0.25 | AGTTTGG{C}{C}A{G}CCCAA | 6 |
| ALB | Primer Forward | 200 | 0.5 | TGAAACATACGTTCCCAAAGAGTTT | 7 |
| | Primer Reverse | 200 | 0.5 | CTCTCCTTCTCAGAAAGTGTGCATAT | 8 |
| | Probe (Cy5) | 100 | 0.25 | TGCTGAAACATTCACCTTCCATGCA | 9 |

d. PCR Mix

PCR reactions were performed using Perfecta® Multiplex qPCR ToughMix® (Quanta Biosciences, Beverly, MA, USA), at a final concentration of 1×. 0.1 μM of fluorescein (VWR International, Fontenay-sous-Bois, France) is added in the PCR mix.

PCR mix assembly is the following:

Perfecta® qPCR Multiplex ToughMix® (1×)

Fluorescein (0.1 μM)

Oligonucleotides BRAF V600 WT, FAM fluorophore (1×)

Oligonucleotides EGFR L858 WT, HEX fluorophore (1×)

Oligonucleotides ALB, Cy5 fluorophore (1×)

Water

TABLE 2

| | "Initial concentration" (cp/μL) | "Final concentration" (cp/μL) | PCR Reaction (μL) |
|---|---|---|---|
| Perfecta qPCR Multiplex ToughMix (x) | 5 | 1 | 5.40 |
| Oligos (x) | 40 | 1 | 0.68 |
| Fluoresceine (μM) | 1 | 0.1 | 2.70 |
| ADN hgDNA | 60606.1 | 3000 | 1.34 |
| Water | | | 16.90 |
| Total - Final volume (μL) | | | 27.02 |

The samples are obtained by dilution of the target sequences in the PCR mix so that the expected final concentration of each target sequence in the non-sonicated case is 3000 cp/μL, as explained in Table 2.

e. dPCR Experiment

The samples are loaded in the inlet chambers of Sapphire chips (Stilla Technologies, Villejuif, France), 27 μL volume loaded per chamber. Three replicates are used per sonicated sample (three chambers per sample). One non-sonicated sample is loaded in triplicate in three independent chambers.

Naica™ Geode (Stilla Technologies, Villejuif, France) is programmed to partition the sample.

The PCR conditions are as follows: 95° C. for 10 minutes, followed by 45 cycles of 95° C. for 30 seconds and 58° C. for 15 seconds.

The exposure times set by default for image acquisition with the Naica™ Prism3 (Stilla Technologies, Villejuif, France) for the Blue, Green, and Red channels are 65 ms, 250 ms, and 50 ms respectively.

f. Correction Factors Calculation

Figure 2:
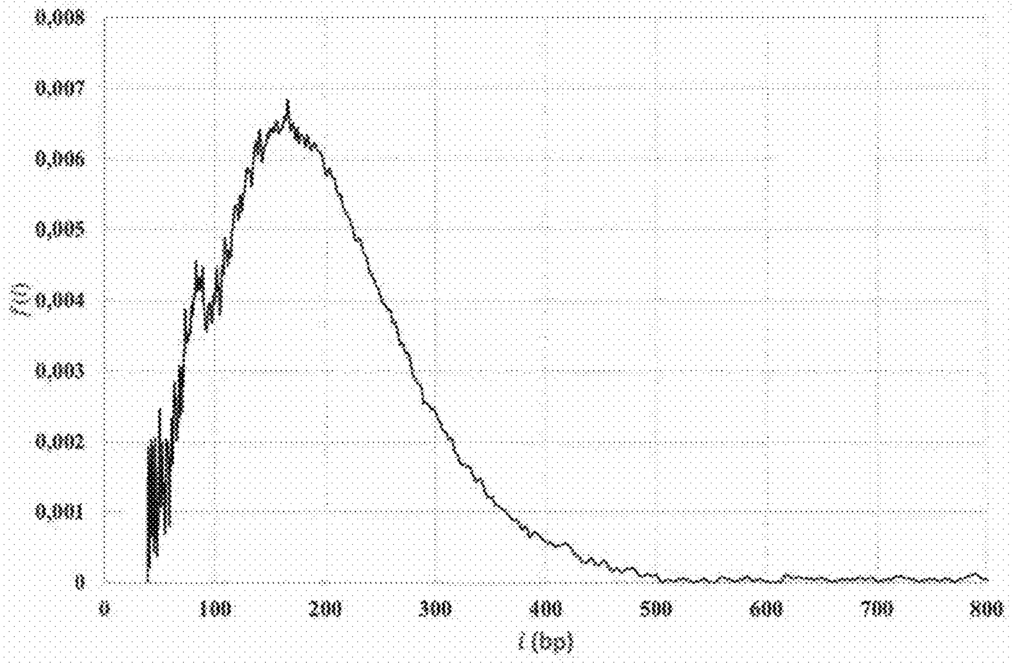
FIG. 2 is a graph showing the length distribution (LD) of DNA fragments in the sample used in Example E1 for a length distribution centered around 150 bp. f(i) is the probability (Y axis-arbitrary unit) that a fragment in the sample has a length of i base pairs (X-axis).

The predicted correction factor according to the method of the invention ("Prediction") is calculated from the fragment length distribution of the sample, experimentally measured, as shown on FIG. 2 for a length distribution centered around 150 bp, and from the length in base pairs (bp) of the sequence to be amplified.

Figure 3:
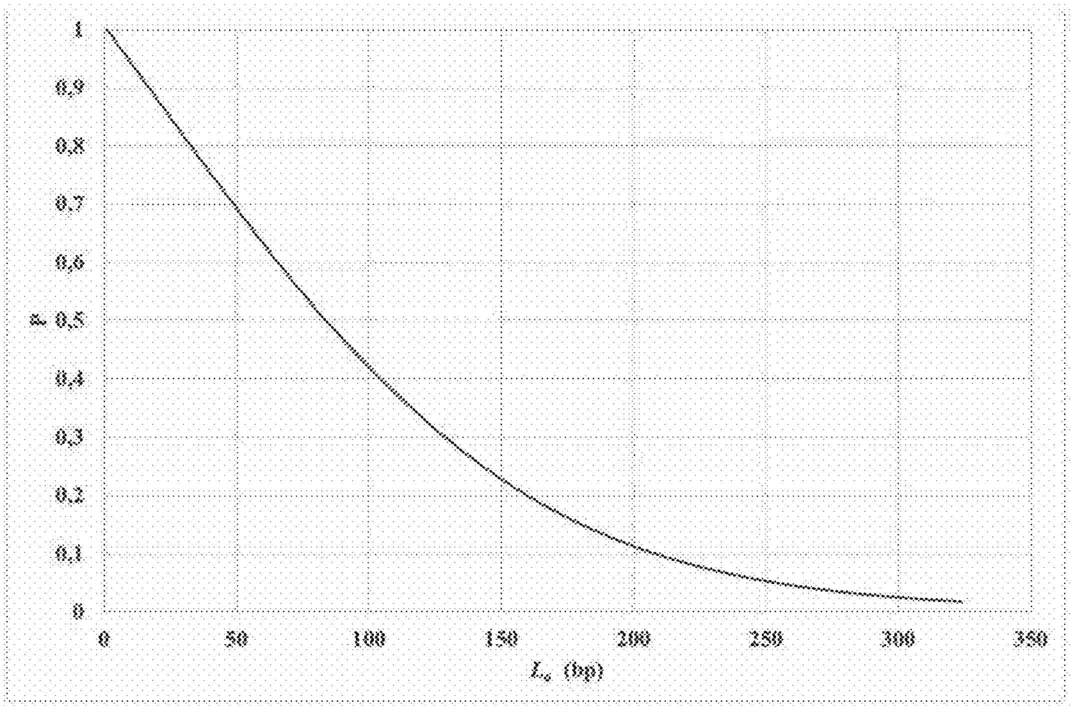
FIG. 3 displays the probability P that the sequence to be amplified is not cut as a function of the length $L_a$ of the sequence to be amplified (in base pairs bp), estimated for the sample shown in FIG. 2.
Figure 4:
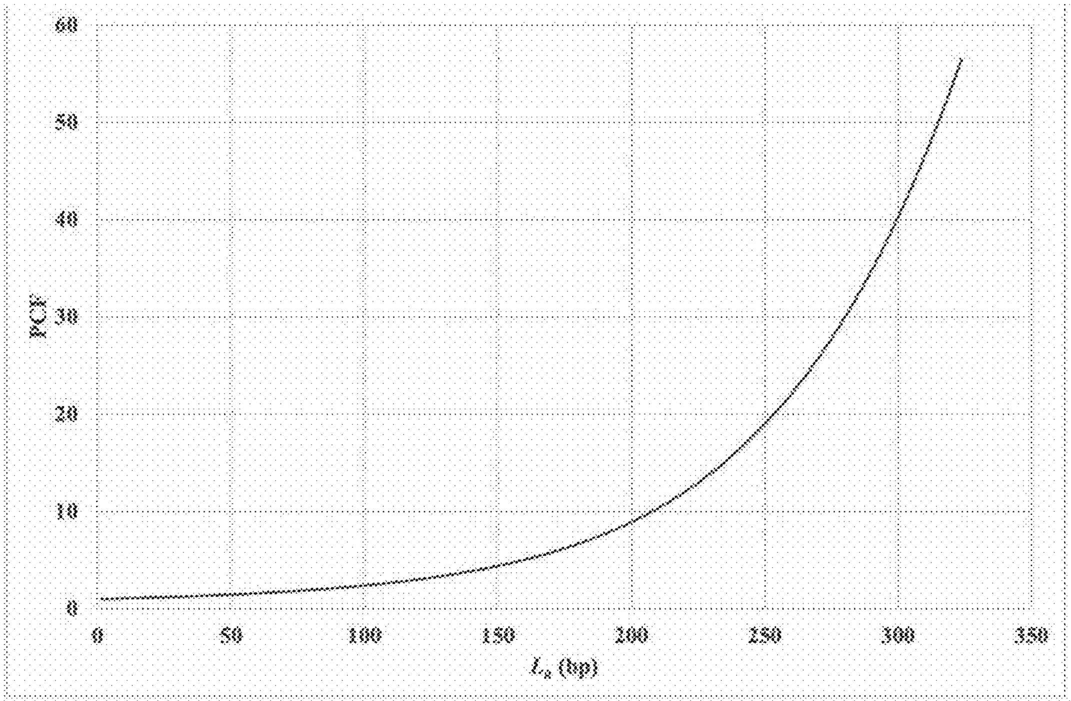
FIG. 4 displays predicted correction factor (PCF) as a function of the length $L_a$ of the sequence to be amplified (in base pairs bp), estimated for the sample shown in FIG. 2.

Computing the correction factor according to the method of the invention requires the probability that the sequence to be amplified is not cut, as a function of the length of the sequence to be amplified, as shown on FIG. 3 for length distribution centered around 150 bp. The correction factor for the same conditions is shown in FIG. 4.

The ground-truth correction factor ("Ground-truth") is obtained in vitro by computing the ratio between the concentration of the detected sequence experimentally measured in the non-sonicated sample versus the sonicated sample.

The relative error ("Relative error") is defined as the error of the predicted correction factor with respect to the ground-truth correction factor.

Results for Example 1

The experimental and theoretical results are compared in Table 3. Predicted and ground-truth correction factors obtained with TriPlex digital PCR experiments measuring the concentration of sequences to be amplified with different sequence lengths (78 bp, 81 bp, 117 bp) in sonicated samples at different fragment lengths (150 bp, 200 bp, 350 bp, 550 bp). Each experimental measure was performed in triplicate and the displayed values are averages of the triplicate values.

TABLE 3

| | | Correction Factor | | |
|---|---|---|---|---|
| | | Sequence to be amplified of length 117 bp | Sequence to be amplified of length 81 bp | Sequence to be amplified of length 78 bp |
| Sonication ordered at 150 bp | Prediction | 2.94 | 1.93 | 1.87 |
| | Ground-truth | 2.51 | 1.67 | 1.64 |
| | Relative error | 15% | 13% | 12% |
| Sonication ordered at 200 bp | Prediction | 2.28 | 1.68 | 1.64 |
| | Ground-truth | 1.93 | 1.50 | 1.46 |
| | Relative error | 15% | 11% | 11% |
| Sonication ordered at 350 bp | Prediction | 1.57 | 1.34 | 1.33 |
| | Ground-truth | 1.31 | 1.18 | 1.16 |
| | Relative error | 17% | 12% | 13% |
| Sonication ordered at 550 bp | Prediction | 1.28 | 1.18 | 1.17 |
| | Ground-truth | 1.18 | 1.17 | 1.16 |
| | Relative error | 8% | 1% | 1% |

It can be seen that the obtained relative error values ranging from 1% to 17% show that the predicted correction factors are consistently accurate and present a slight overestimation with respect to the ground-truth correction factors.

From the above it can be inferred that the method of the invention provides directly useable outcomes in real-life conditions since the lengths of the sequences to be amplified are representative of standard PCR sequences, and since the fragment length distributions are in line with naturally occurring fragmentation.

The invention claimed is:

1. A method of determining the concentration of a detected sequence in non-fragmented nucleic acids comprising the following steps:

i. determining a length distribution (LD) of nucleic acids in a sample comprising fragmented nucleic acids, wherein the fragmented nucleic acids are derived from said non-fragmented nucleic acids;

ii. measuring the concentration of said detected sequence in said sample comprising fragmented nucleic acids with a measuring method, wherein measuring the concentration of the detected sequence comprises amplifying a sequence to be amplified comprising the detected sequence, and iii. correcting the measured concentration of said detected sequence in the sample comprising fragmented nucleic acids with a correction coefficient to obtain the concentration of said detected sequence in non-fragmented nucleic acids, wherein the correction coefficient is based on the length distribution (LD) and at least one parameter of the measuring method, wherein the at least one parameter of the measuring method comprises length of the sequence to be amplified (La), wherein the correction coefficient is determined by using the formula:

$$\frac{1}{\frac{1}{\hat{l}}\left[\left(\sum_{i=L}^{\infty}\mathrm{if}(i)\right)+(1-L)\sum_{i=L}^{\infty}\mathrm{if}(i)\right]};$$

wherein: L is the length of the sequence to be amplified (La), L is ($L_a$−n) with n being an integer from 1 to 15, or L is (r·La) with r being at least 0.75 and less than 1 with the proviso that r·La is always an integer value;

wherein f(i) Where, wherein L is the length of the sequence to be amplified (La);

wherein f(i) is the probability that a fragment in the sample has a length of i base pairs; and wherein $$\hat{l}=\sum_{i=L}^{\infty}\mathrm{if}(i)$$

is the average length of the nucleic acid fragments.

2. The method of claim 1, wherein the correcting is applied if at least 5% of the nucleic acids in the sample have a length shorter than the length of the sequence to be amplified.

3. The method of claim 1, wherein the length of the sequence to be amplified is longer than 40 bp and shorter than 200 bp.

4. The method of claim 1, wherein the length distribution (LD) of nucleic acid fragments in the sample is comprised in a range of from 25 bp to 350 bp.

5. The method of claim 1, wherein the method does not comprise a step of fragmenting the non-fragmented nucleic acids to generate the sample comprising fragmented nucleic acids.

6. The method of claim 1, wherein the method does not comprise assembly of the fragmented nucleic acids into a contiguous sequence.

7. The method of claim 1, wherein the method does not comprise obtaining or predicting the genetic coordinates of the fragmented nucleic acids.

8. The method of claim 1, wherein the method does not comprise obtaining the sequence of the fragmented nucleic acids.

9. The method of claim 1, wherein said measuring method is an isothermal quantitative nucleic acid amplification method.

10. The method of claim 1, wherein the measuring method is a non-isothermal quantitative nucleic acid amplification method.

11. The method of claim 1, wherein the method further comprises:

i. measuring the concentration of a second detected sequence in said sample comprising fragmented nucleic acids with a measuring method, wherein measuring the concentration of the second detected sequence comprises amplifying a second sequence to be amplified comprising the second detected sequence; and ii. correcting the measured concentration of said second detected sequence in the fragmented nucleic acids with a correction coefficient to obtain the concentration of said second detected sequence in non-fragmented nucleic acids, wherein the correction coefficient is based on the length distribution (LD) and at least one parameter of the measuring method;

wherein the length of the sequence to be amplified is different from the length of the second sequence to be amplified.

12. The method of claim 11, wherein the measuring method comprises a multiplex amplification step.

13. The method of claim 1, wherein the sample comprising fragmented nucleic acids is a naturally fragmented sample.

14. The method of claim 1, wherein the sample comprising fragmented nucleic acids is an artificially fragmented sample.

15. The method of claim 1, wherein the correction coefficient is determined by using the formula:

$$\frac{1}{\frac{1}{\hat{l}}\left[\left(\sum_{i=L}^{\infty} if(i)\right) + (1-L)\sum_{i=L}^{\infty} f(i)\right]};$$

wherein: L is the length of the sequence to be amplified ($L_a$), L is ($L_a$−n) with n being an integer from 1 to 15, or L is ($r \cdot L_a$) with r being at least 0.75 and less than 1 with the proviso that r·La is always an integer value;

wherein f(i) is the probability that a fragment in the sample has a length of i base pairs;

wherein $$\hat{l} = \sum_{i=1}^{\infty} if(i)$$

is the average length of the nucleic acid fragments; and wherein the correcting comprises multiplying the concentration measured in the sample comprising fragmented nucleic acids with the correction coefficient.

16. The method of claim 15, wherein L is the length of the sequence to be amplified ($L_a$).

17. A system configured to determine the concentration of a detected sequence in non-fragmented nucleic acids comprising i. an amplification module configured for measuring the concentration of said detected sequence in a sample comprising fragmented nucleic acids, said fragmented nucleic acids being derived from said non-fragmented nucleic acids;

ii. a module configured to compute a correction coefficient depending on a length distribution (LD) of nucleic acids in the sample and on at least one parameter of said measuring, wherein the at least one parameter includes the length of a sequence to be amplified (La) comprising the deleted sequence; and iii. a module configured to compute the concentration of said detected sequence in non-fragmented nucleic acids with said correction coefficient, wherein the correction coefficient is determined by using the formula:

$$\frac{1}{\frac{1}{\hat{l}}\left[\left(\sum_{i=L}^{\infty} if(i)\right) + (1-L)\sum_{i=L}^{\infty} if(i)\right]};$$

wherein: L is the length of the sequence to be amplified (La), L is ($L_a$−n) with n being an integer from 1 to 15, or L is (r·La) with r being at least 0.75 and less than 1 with the proviso that r·La is always an integer value;

wherein f(i) Where, wherein L is the length of the sequence to be amplified (La);

wherein f(i) is the probability that a fragment in the sample has a length of i base pairs; and wherein $$\hat{l} = \sum_{i=L}^{\infty} if(i)$$

is the average length of the nucleic acid fragments.

18. The system configured to determine the concentration of a detected sequence in non-fragmented nucleic acids according to claim 17, amplification wherein the module configured for measuring the concentration of said detected sequence in said fragmented nucleic acids is an isothermal quantitative nucleic acid amplification module, selected from loop mediated isothermal amplification module and quantitative nucleic acid sequence-based amplification module.

19. The system configured to determine the concentration of a detected sequence in non-fragmented nucleic acids according to claim 17, amplification wherein the module configured for measuring the concentration of said detected sequence in said fragmented nucleic acids is a non-isothermal quantitative nucleic acid amplification module, selected from quantitative Polymerase Chain Reaction module, real time Polymerase Chain Reaction module, digital Polymerase Chain Reaction module, multiplex Polymerase Chain Reaction module and multiplex digital Polymerase Chain Reaction module.

* * * * *

SEQUENCE LISTING

```
<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: BRAF V600 WT - Primer Forward

<400> SEQUENCE: 1

tactgttttc ctttacttac tacacctcag                                    30


<210> SEQ ID NO 2
<211> LENGTH: 21
<212> TYPE: DNA
<213> ORGANISM: Artificial Sequence
<220> FEATURE:
<223> OTHER INFORMATION: BRAF V600 WT - Primer Reverse

<400> SEQUENCE: 2

actgatggga cccactccat c                                             21


<210> SEQ ID NO 3
<211> LENGTH: 20
<212> TYPE: DNA
<213> ORGANISM: Artificial Sequence
```

-continued

<220> FEATURE:
<223> OTHER INFORMATION: BRAF V600 WT - Probe (FAM)
<220> FEATURE:
<221> NAME/KEY: modified_base
<222> LOCATION: 10
<223> OTHER INFORMATION: /mod_base="OTHER"
/note="Locked Nucleic Acid (LAN) base"
<220> FEATURE:
<221> NAME/KEY: modified_base
<222> LOCATION: 11
<223> OTHER INFORMATION: /mod_base="OTHER"
/note="Locked Nucleic Acid (LAN) base"

<400> SEQUENCE: 3
ctagctacag tgaaatctcg 20

<210> SEQ ID NO 4
<211> LENGTH: 23
<212> TYPE: DNA
<213> ORGANISM: Artificial Sequence
<220> FEATURE:
<223> OTHER INFORMATION: EGFR L858 WT - Primer Forward

<400> SEQUENCE: 4
gcagcatgtc aagatcacag att 23

<210> SEQ ID NO 5
<211> LENGTH: 25
<212> TYPE: DNA
<213> ORGANISM: Artificial Sequence
<220> FEATURE:
<223> OTHER INFORMATION: EGFR L858 WT - Primer Reverse

<400> SEQUENCE: 5
cctccttctg catggtattc tttct 25

<210> SEQ ID NO 6
<211> LENGTH: 16
<212> TYPE: DNA
<213> ORGANISM: Artificial Sequence
<220> FEATURE:
<223> OTHER INFORMATION: EGFR L858 WT - Probe (HEX)
<220> FEATURE:
<221> NAME/KEY: modified_base
<222> LOCATION: 8
<223> OTHER INFORMATION: /mod_base="OTHER"
/note="Locked Nucleic Acid (LAN) base"
<220> FEATURE:
<221> NAME/KEY: modified_base
<222> LOCATION: 9
<223> OTHER INFORMATION: /mod_base="OTHER"
/note="Locked Nucleic Acid (LAN) base"
<220> FEATURE:
<221> NAME/KEY: modified_base
<222> LOCATION: 11
<223> OTHER INFORMATION: /mod_base="OTHER"
/note="Locked Nucleic Acid (LAN) base"

<400> SEQUENCE: 6
agtttggcca gcccaa 16

<210> SEQ ID NO 7
<211> LENGTH: 25
<212> TYPE: DNA
<213> ORGANISM: Artificial Sequence
<220> FEATURE:
<223> OTHER INFORMATION: ALB - Primer Forward

<400> SEQUENCE: 7
tgaaacatac gttcccaaag agttt 25

-continued

```
<210> SEQ ID NO 8
<211> LENGTH: 26
<212> TYPE: DNA
<213> ORGANISM: Artificial Sequence
<220> FEATURE:
<223> OTHER INFORMATION: ALB - Primer Reverse

<400> SEQUENCE: 8

ctctccttct cagaaagtgt gcatat                                          26

<210> SEQ ID NO 9
<211> LENGTH: 25
<212> TYPE: DNA
<213> ORGANISM: Artificial Sequence
<220> FEATURE:
<223> OTHER INFORMATION: ALB - Probe (Cy5)

<400> SEQUENCE: 9

tgctgaaaca ttcaccttcc atgca                                           25
```